(12) United States Patent
Anderson et al.

(10) Patent No.: US 7,497,901 B2
(45) Date of Patent: Mar. 3, 2009

(54) TUNGSTATE AND MOLYBATE WOOD PRESERVATIVES

(75) Inventors: Albert Gordon Anderson, Wilmington, DE (US); John Feaster, Chesapeake City, MD (US); Damini Patel, Wallingford, PA (US); Mark Scialdone, West Grove, PA (US)

(73) Assignee: E. I. dupont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/643,595

(22) Filed: Dec. 21, 2006

(65) Prior Publication Data

US 2007/0163466 A1 Jul. 19, 2007

Related U.S. Application Data

(60) Provisional application No. 60/755,213, filed on Dec. 30, 2005.

(51) Int. Cl.
| | |
|---|---|
| A01N 59/16 | (2006.01) |
| A01N 59/20 | (2006.01) |
| A01N 31/08 | (2006.01) |
| A01N 31/00 | (2006.01) |
| B05D 5/00 | (2006.01) |
| B05D 7/06 | (2006.01) |
| B05D 1/02 | (2006.01) |
| B05D 1/18 | (2006.01) |
| B05D 1/28 | (2006.01) |
| B05D 3/00 | (2006.01) |
| B32B 21/04 | (2006.01) |
| B32B 21/06 | (2006.01) |

(52) U.S. Cl. .............. 106/18.32; 106/15.05; 252/399; 252/400.52; 252/400.54; 252/405; 252/407; 424/78.08; 424/78.09; 424/405; 424/617; 424/630; 424/638; 424/641; 427/297; 427/351; 427/421.1; 427/428.01; 427/429; 427/439; 427/440; 428/375; 428/532; 428/537.1; 428/537.5; 514/494; 514/500; 514/690

(58) Field of Classification Search .............. 106/15.05, 106/18.32; 252/399, 400.52, 400.54, 405, 252/407; 424/78.08, 78.09, 405, 617, 630, 424/638, 641; 427/297, 351, 421.1, 428.01, 427/429, 439, 440; 428/375, 532, 537.1, 428/537.5; 514/492, 494, 500, 690
See application file for complete search history.

(56) References Cited

U.S. PATENT DOCUMENTS

| | | | |
|---|---|---|---|
| 3,404,135 A | 10/1968 | Tietz | |
| 3,706,704 A | 12/1972 | Heilman | |
| 4,175,090 A | 11/1979 | Berry | |
| 4,409,358 A | 10/1983 | Kraft et al. | |
| 4,504,468 A | 3/1985 | Brill et al. | |
| 4,656,192 A | 4/1987 | Yamato | |
| 4,737,491 A | 4/1988 | Leppavuori et al. | |
| 4,988,545 A * | 1/1991 | Laks | 427/440 |
| 5,242,685 A | 9/1993 | Ruppersberger et al. | |
| 6,197,763 B1 | 3/2001 | Hepworth Thompson et al. | |
| 6,541,038 B1 | 4/2003 | Tanaka et al. | |
| 6,787,675 B2 | 9/2004 | Pan et al. | |
| 6,843,837 B2 | 1/2005 | Zhang et al. | |
| 6,924,398 B2 | 8/2005 | Pan et al. | |
| 6,978,724 B2 | 12/2005 | Anderson et al. | |
| 7,259,187 B2 | 8/2007 | Kagechika | |
| 2005/0000387 A1* | 1/2005 | Wang et al. | 106/18.32 |
| 2005/0107467 A1* | 5/2005 | Richardson | 514/499 |
| 2007/0157847 A1* | 7/2007 | Anderson et al. | 106/18.32 |
| 2007/0163465 A1* | 7/2007 | Anderson et al. | 106/12 |
| 2007/0169664 A1 | 7/2007 | Anderson | |

FOREIGN PATENT DOCUMENTS

| | | |
|---|---|---|
| AU | 614386 | 8/1991 |
| EP | 0 111 995 A2 | 6/1984 |
| EP | 137126 | 4/1985 |
| EP | 238 413 | 9/1987 |
| EP | 0 565 266 | 10/1993 |
| EP | 0728 478 | 8/1996 |
| FR | 2 668 031 | 4/1992 |
| JP | 1299291 | 12/1989 |
| JP | 02/006402 | 1/1990 |
| JP | 7069825 | 3/1995 |
| JP | 7126111 | 5/1995 |
| JP | 8-12504 A * | 1/1996 |
| JP | 10291205 A | 4/1997 |
| JP | 9-175916 | 7/1997 |
| JP | 09175916 | 7/1997 |
| JP | 10-45518 A * | 2/1998 |
| JP | 2000/141316 | 5/2000 |
| JP | 2001/097808 | 4/2001 |
| JP | 2001-310302 A | 11/2001 |

(Continued)

OTHER PUBLICATIONS

U.S. Appl. No. 60/755,213, filed Dec. 30, 2005, Anderson et al.*
U.S. Appl. No. 61/014,812, filed Dec. 19, 2007, Anderson et al.*
U.S. Appl. No. 61/014,820, filed Dec. 19, 2007, Anderson et al.*
U.S. Appl. No. 61/014,827, filed Dec. 19, 2007, Anderson et al.*
U.S. Appl. No. 61/014,830, filed Dec. 19, 2007, Anderson et al.*
U.S. Appl. No. 61/014,841, filed Dec. 19, 2007, Anderson et al.*
U.S. Appl. No. 60/755,211, filed Dec. 30, 2005, Albert Anderson.
U.S. Appl. No. 60/755,214, filed Dec. 30, 2005, Albert Anderson.
U.S. Appl. No. 60/755,242, filed Dec. 30, 2005, Albert Anderson.
W. J. Brill et. al., Termite Killing by Molybdenum and Tungsten Compounds, Naturwissenschaften, 1987, vol. 74:494-495.

(Continued)

Primary Examiner—Anthony J. Green

(57) ABSTRACT

Complexes of copper and/or zinc with molybdate and/or tungstate were solubilized in ammonia or ammoniacal solution providing preservative solutions that fully penetrate wood. With loss of the ammonia from the wood, the complexes were stably retained in the wood providing a long lasting preservative.

71 Claims, No Drawings

FOREIGN PATENT DOCUMENTS

| | | |
|---|---|---|
| JP | 2003137702 | 5/2003 |
| JP | 2003-334804 A | 11/2003 |
| JP | 2004-043327 A | 2/2004 |
| JP | 49055829 A | 4/2005 |
| JP | 01038203 A | 1/2006 |
| WO | 2000/19827 | 4/2000 |
| WO | WO 00/19827 A1 * | 4/2000 |
| WO | WO 2004/041491 | 5/2004 |

OTHER PUBLICATIONS

Jennifer Cowan et al., Leaching Studies and Fungal Resistance of Potential New Wood Perservatives, Forest Products Journal, 2005, vol. 55:66.

John M. Black et. al., Inorganic Surface Treatments for Weather-Resistant Natural Finishes, Forest Service Research Paper, 1974, vol. 232:40.

Mounir Baya et al., Fungicidal Activity of Beta-Thujaplicin Analogues, Pest Management Science, vol. 57:833-838, 2001 (no month).

Connick et al., (2001) Environmental Entomology, V30, pp. 449-455 (no month).

Carol A. Clausen: "Report #IRG/WP 96-10 160: Ibuprofen Inhibits in Vitro Growth of Brown-Rot Fungi" (1996) International Research Group on Wood Preservation, Stockhold, Sweden, (no month).

A Trinchero et al., "Spectroscopic Behavior of Copper Complexes of Non-Steroidal Anti-Inflammatory Drugs" Biopolymers, vol. 74, (2004), pp. 120-124 (no month).

S. Dutta et al., "Structural Characterization and Sod Activity of Copper-Oxaprozinate," Inorganic Chemistry Communications, Elsevier, Amsterdam, NL, vol. 7, No. 9 (Sep. 2004), pp. 1071-1074.

International Search Report, Application No. PCT/US2006/049542, Written Opinion of the International Searching Authority (Aug. 15, 2007).

International Search Report, Application No. PCT/US2006/049543, Written Opinion of the International Searching Authority (Jul. 18, 2007).

International Search Report, Application No. PCT/US2006/049541, Written Opinion of the International Searching Authority (Aug. 20, 2007).

International Search Report, Application No. PCT/US2006/049544, Written Opinion of the International Searching Authority, International Filing Date Dec. 28, 2006.

Chemical Abstract No. 47:8673, abstract of an article by Bryant et al entitled "Formation Constants of Some Metal-Tropolone Complexes", Nature (1952), 170, 247-8 [no month].

Chemical Abstract No. 47:65435, abstract of an article by Bryant et al entitled "Formation Constants of Metal Complexes of Tropolone and Its Derivatives", Journal of the American Chemical Society (1953), 75, 3784-6 [no month].

Chemical Abstract No. 48:41860, abstract of an article by Bryant et al entitled "Formation Constants of Metal Complexes of Tropolone and Its Derivatives", Journal of The American Chemical Society (1954), 76, 1696-7 [no month].

* cited by examiner

TUNGSTATE AND MOLYBATE WOOD PRESERVATIVES

This application claims the benefit of U.S. Provisional Application No. 60/755,213, which is incorporated in its entirety as a part hereof for all purposes.

TECHNICAL FIELD

This invention relates to preservatives for wood and other cellulosic materials. Specifically, protection of cellulosic materials is provided by the application of solutions of copper and/or zinc complexes with tungstate or molybdate. These complexes readily penetrate the cellulosic materials.

BACKGROUND

The decay of wood and other cellulosic materials by fungi, and the consumption of wood by termites, cause significant economic loss. Until recently, the most widely used wood preservative has been chromated copper arsenate (CCA). However, production of CCA for use in residential structures was prohibited as of January 2004 due to issues raised concerning the environmental impact and safety of arsenic and chromium used in CCA-treated lumber. As CCA replacements, arsenic-free and chromium-free wood preservatives are sought. Retention in treated wood of copper and other metal ions that are effective fungicides in treated wood is a challenge. Metal salts are generally water-soluble and rapidly leach from treated wood, which causes loss of the preservative function.

Tungstate and molybdate ions are toxic to termites, shipworms, and other wood-eating pests. Compounds containing these ions disrupt the symbiotic relationship between the wood-eating pest and the microbes in its gut which break down cellulose and fix nitrogen providing nutrients to the host. Nitrogenase, the microbial enzyme involved in nitrogen fixation, is a molybdenum-containing enzyme. It is known that tungstate can compete with molybdate to prevent microbial nitrogen fixation. Thus molybdate and tungstate toxicity to termites is thought to be related to nitrogenase, nitrogen fixation, and secondarily to cellulose degradation, related to microbial symbionts in the gut of the wood-eating pest.

Various molybdate and tungstate compounds have been used as termiticides. Sodium molybdate and sodium tungstate have been shown to be effective in termite killing baits (Brill et al., Naturwissenschaften v 74 p 494-495 (1987); JP 2001/097808 A). However, these compounds are too water soluble to provide a long lasting wood preservative. Treatment of wood surfaces with various inorganic compounds including copper molybdate in an aqueous mix has been described (Black and Mraz, Forest Service Research Paper, v 232 p 40 (1974); JP 2000/141316). The surface coating is not sufficient for wood protection.

U.S. Pat. No. 4,504,468 discloses treatment of cellulosic material for termite control with soluble metal salts of molybdate and tungstate. However, being soluble, these compounds leach from the treated material and therefore do not provide a lasting preservative.

JP-A 02/006,402 discloses a two-step process for retaining molybdate and tungstate in a cellulose based material. In the first step, wood is impregnated with a water soluble molybdic acid salt and/or tungstic acid salt, followed in a second step by addition of an inorganic acid or acid salt to reduce the solubility of the molybdate or tungstate ions. This two step process is very cumbersome and costly for commercial use.

Reduced leaching was obtained in using preservatives by replacing the arsenate of CCA with molybdate or tungstate (Cowan and Banerjee, Forest Products Journal v 55 p 66 (2005)). The toxicity of the chromium salts in these preservatives remains an issue in disposal of treated wood by incineration.

EP-B1 238,413 discloses a wood preservative containing a quaternary ammonium salt having wood preservative property, a water soluble inorganic and/or organic copper salt, ammonia and/or a water soluble amine capable of forming a complex with copper ions, and a molybdic acid compound and/or a nitrite. A quaternary ammonium salt is very costly for commercial use in wood preservatives since no method is provided to retard leaching loss of the very soluble quaternary ammonium salt.

U.S. Pat. No. 4,409,358 discloses a crop protection agent that is a copper amine salt of a polymer or copolymer of acrylic acid and/or methacrylic acid and optionally a lower alkyl ester of acrylic acid or methacrylic acid. U.S. Pat. No. 5,242,685 discloses a crop protection agent for controlling fungi or bacteria that is an aqueous solution of a polymer acid, containing acrylic acid or methacrylic acid and optionally acrylate or methacrylate, and at least 12% of copper, where the copper is dissolved by applying ammonia gas under pressure. The expense in making acrylic acid or methacrylic acid, and the requirement for 2 moles of monobasic (meth)acrylic acid groups per mole of Cu make this type of agent undesirable for commercial preparation.

U.S. Pat. No. 4,175,090 discloses a process for preparing a solution containing a cuprammonium complex of one or more $C_1$ to $C_4$ monocarboxylic acids. This type of complex would readily leach from treated wood and thus not provide a lasting preservative.

There remains a need for wood preservatives that are highly penetrating, effective, long lasting, and easily prepared for replacement of the CCA wood preservative.

SUMMARY

One embodiment of this invention provides an aqueous composition comprising in admixture (a) a complex that comprises (i) molybdate ions, tungstate ions or a mixture thereof, and (ii) copper ions, zinc ions or a mixture thereof; and (b) ammonia and/or ethanolamine; wherein component (b) is present in an amount sufficient to solubilize the complex; and wherein a molybdate ion, when present in component (a), is present in the absence or substantial absence of a quaternary ammonium salt.

Another embodiment of this invention provides a process for preparing a composition by combining the components (a) and (b) described above, and solubilizing a complex as formed therefrom.

A further embodiment of this invention provides a process for preserving cellulosic material, or an article that comprises cellulosic material, comprising contacting the cellulosic material or the article with the composition described above.

Yet another embodiment of this invention provides cellulosic material, or an article comprising cellulosic material, wherein the above described composition is adsorbed on or absorbed in the cellulosic material.

DETAILED DESCRIPTION

A complex that is formed from molybdate and/or tungstate ions, and copper and/or zinc ions, is solubilized by, for example, ammonia or ethanol amine, and is used in such form as a deeply-penetrating and long lasting preservative for wood and other cellulosic materials. As the metal ion complex is solubilized in an aqueous medium, it can be readily adsorbed onto, and/or absorbed or imbibed into, wood or other cellulosic materials. Upon loss or evaporation of the solvent or co-solvents in the solution, the complex becomes insoluble, thereby fixing the molybdate and/or tungstate and the metal ion(s) within the target material, and providing an effective preservative composition for the cellulosic material.

A cellulosic material is preserved in the sense that contact with a composition of this invention protects the material against decay or deterioration from deleterious effects as caused by either or both of pests and living organisms. For example, a composition of this invention protects a cellulosic material against termite attack due to the termiticidal activity of molybdate and/or tungstate, and also provides it with fungal protection due to the fungicidal activity of the copper and/or zinc. The potential for deterioration or destruction of a cellulosic material by exposure to natural conditions or hazards is thus reduced and preferably prevented by the presence in and/or on the material of a composition of this invention. A process of this invention provides preservation for cellulosic materials by providing contact of the materials with a composition of this invention, and thus achieves the benefits of protection against adverse conditions, pests and organisms, such as termites and fungus as described above.

The cellulosic materials that can be treated with a composition of this invention are those that contain or are derived from cellulose, which is a polysaccharide that forms the main constituent of the cell wall in most plants, and is thus the chief constituent of most plant tissues and fibers. These cellulosic materials include wood and wood products such as lumber, plywood, oriented strand board and paper, in addition to lignin, cotton, hemicellulose and cellulose itself. References herein to the preservation of wood by the use of a composition of this invention, or by the performance of a process of this invention, or references to the usefulness of a composition hereof as a wood preservative, should therefore be understood to be references to the preservation of all types of cellulosic materials, not just wood alone.

Molybdate/Tungstate with Copper/Zinc in Solution

Molybdate and tungstate ions used to prepare preservative solutions in this invention may be obtained from any soluble source of molybdate or tungstate, such as potassium molybdate, ammonium molybdate, sodium molybdate dihydrate, molybdenum oxide, molybdic acid, potassium tungstate, ammonium tungstate, sodium tungstate dihydrate, tungsten oxide, or tungstic acid. Additional compounds that may be used as sources of tungstate or molybdate ions include compounds such as silicotungstates, phosphotungstates, borotungstates, silicomolybdates, phosphomolybdates and boromolybdates.

The fungitoxic metals copper and/or zinc, in ionic state, e.g. copper ion, may be used to form complexes with molybdate and/or tungstate ions that are solubilized in to provide a preservative composition according to this invention. Any soluble copper salt may be a source of copper ions, and suitable Cu(II) salts may include, for example, copper sulfate, copper sulfate pentahydrate, cupric chloride, cupric acetate, and copper carbonate. Particularly useful as the copper salt is copper sulfate pentahydrate. Any soluble zinc salt may be a source of zinc ions, and suitable Zn(II) salts may include, for example, zinc sulfate, zinc chloride, zinc acetate, zinc nitrate and zinc carbonate. Particularly useful as the zinc salt is zinc acetate. Mixtures of copper ion sources and zinc ion sources may be used in the compositions of this invention as well.

Sources of molybdate ions, tungstate ions, copper ions and zinc ions, as described above, are available commercially.

To form a composition of this invention, the components thereof are combined in admixture. For example, an aqueous solution may be prepared that contains a molybdate and/or a tungstate salt, and a copper and/or zinc salt or other source of copper ions. The mixture in solution of the salts as described above forms a complex. A complex as used herein is essentially a salt, but may also be described as an association containing organic and/or inorganic components in any combination that is held together by covalent or electrostatic bonds, or by bonds that are intermediate between covalent and electrostatic bonds such as in a coordination compound. One example of the combination of components as mentioned above leads to formation of a complex between a tungstate ion and a copper ion, and the complex precipitates in aqueous solution, as shown in Diagram I:

Diagram I
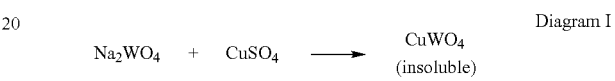

By combining these same components in aqueous mixture containing a solvent or co-solvent such as ammonia, however, the tungstate/copper ion complex is found to remain fully soluble, as shown in Diagram II:

Diagram II
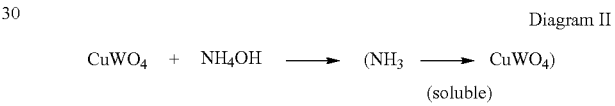

In preparing this solution, it is particularly useful to include ammonium hydroxide in sufficient concentration to preclude the formation of a precipitate while mixing the components. A solvent or co-solvent such as ammonia is present in sufficient amount to maintain solubility of the complex in the aqueous mixture. Typically, ammonia as used to prepare the solution is used in an amount such that it is present at about 0.5% to 3% by weight in the final solution. Preferred is 1.4 wt % ammoniacal water solution. Ethanolamine may be used in an amount of about 0.5% to 3% by weight of the solution as an alternative to ammonia. Additionally, combinations of ethanolamine and ammonia may be used. Although use of ammonia is preferred, other solvents or co-solvents that form a solution with water, that solubilize the complex as readily as ammonia, and also evaporate as readily as ammonia from the cellulosic material after treatment, may also be used in addition to or in place of ammonia or ethanol amine in the solvent system in which the complex is solubilized.

In general, solubility of the complex is determined by visual observation, and a complex is considered to be solubilized when a sufficient amount of the complex is dissolved in the solution to permit a desired amount of the complex to be adsorbed on and/or absorbed in the cellulosic material when the treatment thereof occurs.

Mixtures of molybdate and/or tungstate ions with copper and/or zinc ions are used in the preservative compositions of this invention in amounts effective to provide a desired level of protection in view of the service conditions (including the nature of the target material, the contemplated end use, and the geographic location) that the cellulosic material to be treated will experience. The concentration of molybdate and/or tungstate ions in the treatment solution is thus usually in the range of about 10 to about 6,000 ppm, and sometimes in the range of between about 200 and about 1700 ppm. The copper and/or zinc ions are typically used at a concentration in the treatment solution in the range of about 500 ppm to about 11,000 ppm. Marine use generally requires the higher concentrations, up to about 11,000 ppm while land use may involve concentrations between about 500 and 6,000 ppm. It is particularly useful to include corresponding amounts of molybdate and/or tungstate and copper and/or zinc such that these components are present in a complex in comparable amounts. One method of determining the content of a complex in a treated cellulosic material is to burn the material and analyze the ash for its content of the components that have been used to prepare the complex. A composition hereof may be made by mixing the components in any suitable device, such as a blender or rotating mixer.

Though the preservative compositions of this invention that are used in treating cellulosic materials are largely if not completely dissolved in solutions such as ammoniacal solutions, a more concentrated master batch may be made that is readily transported for commercial purposes, and then diluted prior to use. Such a concentrated master batch may be a slurry, containing partially precipitated molybdate and/or tungstate and copper and/or zinc complexes. The slurry is prepared for use in treatment by increasing the volume of solution by the addition of one or more solvents or co-solvents, for example to a final concentration where ammonia is used in the solvent system and an approximately 1.4 wt % ammoniacal water solution is obtained.

Features of Molybdate and/or Tungstate and Copper and/or Zinc Complexes in Solution as Wood Preservative Compositions The solubility properties of the molybdate and/or tungstate and copper and/or zinc complexes provide specific attributes valuable in a preservative composition for cellulosic materials. These complexes are insoluble in water but are typically well dissolved, if not completely soluble, in a solvent system such as an ammoniacal solution. When the complex is well dissolved in the solution, deep penetration of the preservative solution into a cellulosic material such as wood, well past the surface wood, is obtained. Following penetration, a solvent or co-solvent such as ammonia readily evaporates from the wood, leaving the termiticidal tungstate and/or molybdate and the antifungal metal as a complex in the aqueous wood environment where it becomes precipitated and binds tenaciously to cellulose. Thus, there is little leaching of metal or preservative components from the treated wood.

Additional Components in Preservative Compositions

Preservative compositions of this invention may include additional components. When molybdate is present in the preservative composition, however, it is present in the absence or substantial absence of a quaternary ammonium salt.

A hydrolyzed olefin/maleic anhydride copolymer, such as described in U.S. Provisional Application No. 60/755,211, which is incorporated in its entirety as a part hereof for all purpose, may be added to the composition to enhance copper and/or zinc retention in treated articles. A hydrolyzed olefin/maleic anhydride copolymer forms a complex with copper and/or zinc that is insoluble in water, but has solubility in an ammoniacal solution that is similar to the solubility of the molybdate and/or tungstate/copper and/or zinc complex described above. The complex formed by the copolymer also penetrates a cellulosic material deeply when dissolved in the solution, and is retained in the wood after loss of a solvent or co-solvent such as ammonia. When a hydrolyzed olefin/maleic anhydride copolymer is present as an additional component in a composition of this invention, copper and/or zinc ions are added in sufficient amount such that it/they form complexes with both the and tungstate and/or molybdate and the copolymer.

Hydrolyzed olefin/maleic anhydride copolymers are prepared by hydrolysis, for example using aqueous NaOH, of olefin/maleic anhydride copolymers to form negatively charged carboxylate ions that can complex with copper and zinc ions. Olefins of particular use in the olefin/maleic anhydride copolymers for hydrolysis are octene and styrene. Mixtures of different types of olefin/maleic anhydride copolymers, such as a mixture of octene/maleic anhydride copolymer and styrene/maleic anhydride copolymer may also be used. The synthesis of olefin/maleic anhydride copolymers is known from sources such as U.S. Pat. No. 3,706,704 and U.S. Pat. No. 3,404,135. Olefin/maleic anhydride copolymers suitable for use herein are generally between about 10,000 and about 50,000 in molecular weight.

A preferred process for the synthesis of styrene/maleic anhydride copolymers, which results in copolymers of molecular weight ranging between 20,000 and 100,000, involves the use of a combination of toluene and isopropyl alcohol as both a solvent and as a chain transfer agent. Using this combination, rather than isopropyl alcohol alone, reduces the percent of mono isopropyl maleate ester formed during the polymerization from about 20% to about 1%. In addition, the molecular weight of the copolymer product is increased from about 18,000 when using isopropyl alcohol alone, to over 20,000 when using a toluene:isopropanol ratio of 1:1. Molecular weights of over 90,000 may be achieved using a ratio of 76:4.

Hydrolyzed olefin/maleic anhydride copolymers of up to about 1,000,000 molecular weight may be used in the compositions hereof. When it is desired, however, to provide a concentrated master batch solution that is to be diluted prior to use, copolymers with greater than about 80,000 molecular weight are extremely viscous and therefore difficult to use. Therefore, preferred in the instant invention are olefin/maleic anhydride copolymers with molecular weight below about 80,000. More preferred are copolymers with molecular weights ranging between 2,000 and about 40,000.

In addition, a copper chelating compound, such as is described in U.S. Pat. No. 6,978,724 (which is incorporated in its entirety as a part hereof for all purposes), may be included in a composition hereof to enhance copper retention in treated articles. A suitable copper chelating compound may have a functional group such as one r more of the following: amidoximes, hydroxamic acids, thiohydroxamic acids, N-hydroxyureas, N-hydroxycarbamates, and N-nitroso-alkyl-hydroxylamines. A suitable copper chelating compound forms a complex with copper and/or zinc that is insoluble in water, but has solubility in an ammoniacal solution that is similar to the solubility of the molybdate and/or tungstate/copper and/or zinc complex described above. The complex formed by the chelating compound also penetrates a cellulosic material deeply when dissolved in the solution, and is retained in the wood after loss of a solvent or co-solvent such as ammonia. When a copper chelating compound is present as an additional component in a composition of this invention, copper and/or zinc ions are added in sufficient amount such that it/they form complexes with both the and tungstate and/or molybdate and the chelating compound.

A functional group in a copper chelating compound can be provided by methods such as the following: in an amidoxime, reacting nitrile-containing compounds with hydroxylamine; in a hydroxamic acid, adding hydroxylamine to anhydride groups of copolymers such as styrene/maleic anhydride or octene/maleic anhydride, and forming styrene/N-hydroxymaleamic acid copolymer or octene/N-hydroxymaleamic acid copolymer; in a thiohydroxmic acid, adding hydroxylamine to dithiocarboxylic acids; in a N-hydroxyurea, reacting hydroxylamine with an isocyanate; in a N-hydroxycarbamate, by reacting hydroxylamine with either a linear or cyclic carbonate; and in a N-nitroso-alkyl-hydroxylamine, by nitrosation of alkyl hydroxylamines.

Preferred chelating compounds contain two or more amidoxime and/or hydroxamic acid groups. By acid catalysis, the amidoxime functionality can be readily converted to the corresponding hydroxamic acid functionality in aqueous solution. A convenient route to this preferred class of compounds is by addition of hydroxylamine to the corresponding nitrile compound. Various methods are known for preparing nitrile compounds. A particularly useful method is cyanoethylation, in which acrylonitrile, or other unsaturated nitrile, undergoes a conjugate addition reaction with protic nucleophiles such as alcohols and amines. Preferred amines for cyanoethylation are primary amines, secondary amines having 1 to 30 carbon atoms, and polyethylene amine. Preferably, a cyanoethylation catalyst is used, such as lithium hydroxide, sodium hydroxide, or potassium hydroxide, between about 0.05 mol % and 15 mol % based on unsaturated nitrile.

A wide variety of materials can be cyanoethylated. Cyanoethylates can be derived from the reaction of acrylonitrile with carbohydrates, such as regenerated cellulose, dextran, dextrin, gums (guar, locust bean, honey locust, flame tree, tara, arabic, tragacanth, and karaya); starches (corn, potato, tapioca and wheat); or modified natural polymers such as cellulose xanthate, dimethylthiourethane of cellulose, ethyl cellulose, ethylthiourethane of cellulose, hydroxyethylcellulose, methylcellulose, and phenylthiourethane of cellulose. Other natural polymers that have been cyanoethylated include flax, jute, manila, sisal, and proteins such as blood albumin, casein, gelatin, gluten, soybean protein, wool, corn zein, or materials derived from such natural polymers. Pretreatment of high molecular weight or water-insoluble carbohydrates and starches with enzymes may be used if necessary to increase the solubility of the amidoxime or hydroxamic acid copper complex in an aqueous ammonia, ethanolamine or pyridine solution.

Synthetic polymers such as acetone-formaldehyde condensate, acetone-isobutyraldehyde condensate, methyl ethyl ketone-formaldehyde condensate, poly(allyl alcohol), poly (crotyl alcohol), poly(3-chloroallyl alcohol), ethylene-carbon monoxide copolymers, polyketone from propylene, ethylene and carbon monoxide, poly(methallyl alcohol, poly (methyl vinyl ketone, and poly(vinyl alcohol) have also been cyanoethylated and can also serve as platforms for further modification into metal-binding polymers.

Preferably the cyanoethylates are derived from sucrose and sorbitol. Most preferred is cyanoethylated sorbitol (DS=6.0), called CE-Sorb6.

The nitrile groups of these cyanoethylates or cyanoalkylates can be reacted with hydroxylamine to form the amidoxime or hydroxamic acid. If hydroxylamine hydrochloride is used instead of hydroxylamine, sodium hydroxide, sodium carbonate or ammonium hydroxide may be used to neutralize the hydrochloric acid. Ammonium hydroxide is preferred. The amidoxime of sorbitol can be prepared by hydroxylamine reaction of CE-Sorb6. This amidoxime of sorbitol is particularly useful as an additional component in the preservative compositions of this invention.

In a further embodiment, ibuprofen may be incorporated as an additional component of the compositions of this invention in view of its brown-rot fungicidal activity and termiticidal activity. Ibuprofen suitable for use as an additional component in the compositions hereof are described in U.S. Provisional Application No. 60/755,214, which is incorporated in its entirety as a part hereof for all purposes. Ibuprofen may be supplied as ibuprofen or sodium ibuprofenate. These compounds are soluble in methanol and ethanol but relatively insoluble in water. Ibuprofen forms a complex with copper and/or zinc that is insoluble in water, but has solubility in an ammoniacal solution that is similar to the solubility of the molybdate and/or tungstate/copper and/or zinc complex described above. The complex formed by ibuprofen also penetrates a cellulosic material deeply when dissolved in the solution, and is retained in the wood after loss of a solvent or co-solvent such as ammonia. When ibuprofen is present as an additional component in a composition of this invention, copper and/or zinc ions are added in sufficient amount such that it/they form complexes with both the and tungstate and/or molybdate and ibuprofen.

Ibuprofen or ibuprofenate may be included in a composition hereof in an amount in the range of from about 100 to about 1,000 ppm depending on the service conditions (including the nature of the target material, the contemplated end use, and the geographic location) that the cellulosic material to be treated will experience. Particularly suitable is a concentration of ibuprofen or ibuprofenate in the composition of between about 200 and about 700 ppm.

In a further embodiment, a tropolone may be incorporated as an additional component of the compositions of this invention. Tropolones suitable for use as an additional component in the compositions hereof are described in U.S. Provisional Application No. 60/755,242, which is incorporated in its entirety as a part hereof for all purposes. The term "tropolone" is commonly used to refer to tropolone itself (2-hydroxycyclohepta-2,4,6-trienone) as well as to compounds that are derivatives of tropolone and have similar properties, such as the natural compounds beta-thujaplicin (also known as hinokitiol), gamma-thujaplicin, and beta-dolabrin. Any of these or similar tropolones having antifungal and/or termiticidal activity may be used as additional components in the compositions of this invention.

A tropolone is typically soluble in methanol and ethanol but relatively insoluble in water. A tropolone also forms a complex with copper and/or zinc that is insoluble in water, but has solubility in an ammoniacal solution that is similar to the solubility of the molybdate and/or tungstate/copper and/or zinc complex described above. The complex formed by a tropolone also penetrates a cellulosic material deeply when dissolved in the solution, and is retained in the wood after loss of a solvent or co-solvent such as ammonia. When a tropolone is present as an additional component in a composition of this invention, copper and/or zinc ions are added in sufficient amount such that it/they form complexes with both the and tungstate and/or molybdate and the tropolone.

A tropolone may be included in a composition hereof in an amount in the range of from about 100 to about 1,000 ppm depending on the service conditions (including the nature of the target material, the contemplated end use, and the geographic location) that the cellulosic material to be treated will experience. Particularly suitable is a concentration of a tropolone in the composition of between about 200 and about 700 ppm.

Preservative Treatment

The ammoniacal solution of a tungstate and/or molybdate and copper and/or zinc complex, optionally containing additional preservative components as described above, may be applied on or in a cellulosic material by dipping, brushing, spraying, soaking, draw-coating, rolling, pressure-treating, or other known methods. The composition may be applied to achieve preservation of any cellulosic material, including for example wood, lumber, plywood, oriented strand board, cellulose, hemicellulose, lignin, cotton, and paper. Particularly efficacious is imbibing into wood under the standard pressure treatment process for waterborne preservative systems. A vacuum may be applied before and/or after application of the preservative composition. Removal of air from the wood under vacuum, then breaking the vacuum in the presence of preservative solution, enhances penetration of the solution into the wood.

A particularly useful treatment process for wood is as described below. Wood, either dry or fresh cut and green, is placed in a chamber that is then sealed and evacuated in a regulated cycle which is determined by the species of wood. Generally, for Southern Yellow Pine (SYP) wood, the period of evacuation is about 30 minutes, during which time the pressure within the sealed chamber is brought to a level of about two inches of mercury or less. The evacuated pressure in the chamber can vary from 0.01 to 0.5 atm. The purpose of this step is to remove air, water and volatiles from the wood. The preservative composition is then introduced into the closed chamber in an amount sufficient to immerse the wood completely without breaking the vacuum to the air. Pressurization of the vessel is then initiated and the pressure maintained at a desired level by a diaphragm or other pump for a given period of time. Initially, the pressure within the vessel will decrease as the aqueous composition within the container penetrates into the wood. The pressure can be raised to maintain a desirable level of treatment throughout the penetration period. Stabilization of the pressure within the vessel is an indication that there is no further penetration of the liquid into the wood. At this point, the pressure can be released, the wood allowed to equilibrate with the solution at atmospheric pressure, the vessel drained, and the wood removed. In this part of the process, the pressures used can be as high as 300 psig, and are generally from about 50 to 250 psig.

Articles Incorporating Preservative Compositions

Articles of the instant invention are those having been treated with a preservative composition described herein. Following treatment of articles such as those made from or incorporating wood, lumber, plywood, oriented strand board, paper, cellulose, cotton, lignin, and hemicellulose, the ammonia in the ammoniacal solution of the preservative composition will dissipate. The molybdate and/or tungstate—copper and/or zinc complex is retained on and/or in the article. Additional components, if included in the composition used for treatment, are retained on and/or in the treated articles as well.

Compositions containing components in addition to a molybdate and/or tungstate-copper and/or zinc complex that are particularly suitable for treatment of an article include those that contain hydrolyzed olefin/maleic anhydride copolymers; copper chelating compounds having at least two functional groups selected from amidoximes, hydroxamic acids, thiohydroxamic acids, N-hydroxyureas, N-hydroxycarbamates, and N-nitroso-alkyl-hydroxylamines; ibuprofen; or a tropolone; and mixtures of these components. Particularly useful in such compositions is a copper chelating compound with at least two hydroxamic groups being derived from styrene/maleic anhydride or octene/maleic anhydride, or a copper chelating compound based on an amidoxime of sorbitol.

The process of this invention for treating cellulosic material also includes a step of incorporating the cellulosic material, or a treated article containing the cellulosic material, such as wood, into a structure such as a house, cabin, shed, burial vault or container, or marine facility, or into a consumable device such as a piece of outdoor furniture, or a truss, wall panel, pier, sill or piece of decking for a building.

EXAMPLES

The present invention is further illustrated in the following Examples. It should be understood that these Examples are given by way of illustration and not by way of limitation. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "conc." means concentrated, "sec" means second(s), "ml" means milliliter(s), "L" means liter(s), "g" means gram(s), "mmol" means millimole(s), "mtorr" means millitorr(s), "hr" means hour(s), "min" means minute(s), "mm" means millimeter(s), "cm" means centimeter(s), "nm" means nanometer(s), "Mw" means weight average molecular weight, "Mn" means number average molecular weight, "mw" means molecular weight, "XRF" stands for X-ray fluorescence spectroscopy, "RH" is relative humidity, "MHz" means megahertz, "NMR" means nuclear magnetic resonance, "IR" means infrared, "ICP" means ion couples plasma, "LC/MS means liquid chromatography/mass spectroscopy, "S/S" means stainless steel, and "DS" is degree of substitution, "SD" is standard deviation, "SMA" is styrene/maleic anhydride copolymer, "SMA-NOH" is styrene/N-hydroxymaleamic acid copolymer, "OMA" is octene/maleic anhydride copolymer, "SYP" is "southern yellow pine", an acronym for closely related pine species that includes *Pinus caribaea* Morelet, *Pinus elliottii* Englelm., *Pinus palustris* P. Mill., *Pinus rigida* P. Mill., and *Pinus taeda* L.

"AWPA" is the American Wood-Preserver's Association. AWPA standards are published in the "AWPA Book of Standards", AWPA, P.O. Box 5690, Granbury, Tex. 76049. The protocol for preservation of SYP stakes is based on AWPA Standard, Method E7-01, Sec. 4, 5, 6, and 7 and E11-97. According to AWPA Standard E7-01, the stakes were graded visually according to the following criterion for fungal decay and insect attack as follows:

| Decay Grades | |
|---|---|
| Grade No. | Description of Condition |
| 10 | Sound. |
| 9.5 | Suspicion of decay permitted |
| 9 | Trace decay to 3% of cross section |
| 8 | Decay from 3 to 10% of cross section |
| 7 | Decay from 10 to 30% of cross section |
| 6 | Decay from 30 to 50% of cross section |
| 4 | Decay from 50 to 75% of cross section |
| 0 | Failure |

| Termite Grades | |
|---|---|
| Grade No. | Description of Condition |
| 10 | Sound. |
| 9.5 | 1 to 2 small nibbles permitted |
| 9 | Slight evidence of feeding to 3% of cross section |
| 8 | Attack from 3 to 10% of cross section |
| 7 | Attack from 10 to 30% of cross section |
| 6 | Attack from 30 to 50% of cross section |
| 4 | Attack from 50 to 75% of cross section |
| 0 | Failure |

The termite grades and decay grades are used to report insect damage and wood decay, respectively, in the tables below.

"Gross retention" refers to the amount of treatment liquid remaining in the wood immediately after imbibition. "Retention" refers to the amount of preservative remaining in the wood after the imbibing liquid has been removed from the wood by drying. The amount can be expressed as ppm or as a weight.

A 'witness stake" or "witness sample" is a whole stake, or a portion of a treated stake, that will be retained as a sample for future analysis.

General Methods

All reactions and manipulations were carried out in a standard laboratory fume hood open to the atmosphere. Deionized water was used where water is called for in the subsequent procedures. Sorbitol, AIBN, acrylonitrile, lithium hydroxide monohydrate, hydroxylamine hydrochloride, copper sulfate pentahydrate, and Chromazurol S [1667-99-8] were obtained from Sigma-Aldrich Chemical (Milwaukee, Wis.) and used as received. Concentrated ammonium hydroxide and glacial acetic acid were obtained from EM Science (Gibbstown, N.J.) and used as received. Cyanoethylated sucrose [18307-13-7] and copper acetate monohydrate were obtained from Acros Organics (Geel, Belgium) and used as received. Sucrose was obtained from Pathmark Supermarket (Wilmington, Del.) and used as received.

pH was determined with pHydrion paper from Micro Essential Laboratory (Brooklyn, N.Y.). Degree of substitution (DS) of the cyanoethylate is expressed in terms of equivalents of acrylonitrile used in the cyanoethylation step. IR spectra were recorded using a Nicolet Magna 460 spectrometer. LC/MS analyses were performed using a Micromass LCT instrument. NMR spectra were obtained on a Bruker DRX Avance (500 MHz $^1$H, 125 MHz $^{13}$C) using deuterated solvents obtained from Cambridge Isotope Laboratories. Elemental analyses were performed by Micro-Analytical Inc, Wilmington, Del. Pressure treatment of southern yellow pine wood was performed in a high-pressure lab using stainless steel pressure vessels following the AWPA standard process (AWPA P5-01). XRF analysis was performed on an Axios Wavelength Dispersive X-ray Fluorescence Spectrometer manufactured by Panalytical Inc., Eindhoven, Netherlands.

Chromazurol S Test for Presence of Copper

Treated wood was tested for the presence of copper with Chromazurol S using the method described by AWPA A3-00 Sec. 2. A 0.167% w/w Chromazurol S in 1.67% w/w aqueous sodium acetate solution was sprayed onto a freshly cut treated wood surface. A change from the yellow solution color to a dark blue color in the sprayed area indicates that a minimum of 25 ppm copper is present. Stakes 965 mm (38") long were cut to 457 mm (18") from each end and the remaining 50.8 mm (2") piece (witness piece) in the middle was treated on the freshly cut surface with a solution of Chromazurol-S. When the freshly cut surface turns dark blue on exposure to the solution, it is an indication of complete penetration of the wood by the wood preservative treatment solution.

Dimensions of Wood as per AWPA E17-01 Sec. 4.2.4:

All wood was cut using inch measurements. The wood was cut as accurately as practicable, given that wood will change dimensions with moisture content; the cutting error is estimated to be within one mm in any dimension. Conversions to metric are provided.

Fahlstrom stake: 0.156"×1.5"×10" (4 mm×38 mm×254 mm)

Pre-Decay stakes: ¾"×¾"×38" (19 mm×19 mm×1154 mm)

Decay stake: ¾"×¾×18" (19 mm×19 mm×450 mm)

Depletion stake: 1.5"×1.5"×18" (38 mm×38 mm×450 mm)

Blocks: ¾"×¾"×¾ (19 mm×19 mm×19 mm)

Preparation of Styrene/Maleic Anhydride Copolymer

Styrene/maleic anhydride copolymer (SMA) was prepared as described in co-pending application with filing #60/755,211, which is herein incorporated by reference, as follows:

An 18 L multi-necked flask was equipped with two dropping funnels, reflux condenser, heating mantel, mechanical stirrer, and nitrogen bubbler. The flask was charged with 9500 g (11 L) of toluene and 500 g (640 ml) of isopropanol. To this solution was added 1276 g of maleic anhydride powder. A solution of 15 g of AIBN dissolved in 500 g (578 ml) of toluene was prepared and placed in one of the dropping funnels. The second funnel was charged with 1302.6 g of styrene. The apparatus was sealed and purged with nitrogen. The maleic anhydride solution was warmed to 60° C. and about one-third of the AIBN solution was added. Then about 150 ml of styrene was added to the flask from the funnel. There was about a 5 minute induction period during which oxygen was consumed. After a white precipitate began to form, indicating that the polymerization had begun, the remaining styrene was added in 150 ml portions during 60 minutes. The AIBN solution was added in thirds over 60 minutes. The addition of styrene and AIBN maintained the reaction temperature at about 70° C. to 80° C. without much additional heat from the mantel. After addition was complete, the reaction temperature was maintained at about 80° C. for an additional 2 hours by using the heating mantel. The white slurry of copolymer was then cooled to about room temperature, filtered, washed with warm toluene, and dried in a vacuum oven at 90° C. to obtain 2460 g (95.5% yield) of SMA and 40 g of mono isopropyl maleate. The Mw=40,400 and the Mn=18,600. The washings were evaporated to give an additional 0.4 g of mono isopropyl maleate ($^1$H NMR (CDCl$_3$): δ1.32 (d, J=1.2, CH3, 6H), 5.15 (m, CH, 1H), 6.36 (m, CH, 2H) ppm.

Preparation of Hydrolyzed Octene/Maleic Anhydride Copolymer

A 1:1 co-polymer of octene and maleic anhydride monosodium salt was prepared as described in U.S. Pat. No. 3,706,704 and U.S. Pat. No. 3,404,135. The Mw of the octane/maleic anhydride copolymer (OMA), which is the precursor of hydrolyzed 1:1 octene/maleic anhydride copolymer monosodium salt, was determined by size exclusion chromatography to be 8595+/−50. The resulting co-polymer was hydrolyzed with aqueous sodium hydroxide solution and brought to a 27.1% w/w solution in water.

Preparation of CE-Sorb6: Cyanoethylation of Sorbitol

A 1000 ml 3-necked round-bottomed flask equipped with an mechanical stirrer, reflux condenser, nitrogen purge, dropping funnel, and thermometer was charged with water (18.5 ml) and lithium hydroxide monohydrate (1.75 g) and the first portion of sorbitol (44.8 g). The solution was heated to 42° C. with a water bath with stirring and the second portion of sorbitol (39.2 g) was added directly to the reaction flask. The first portion of acrylonitrile (100 ml) was then added to the reaction drop-wise via a 500 ml addition funnel over a period of 2 hr. The reaction was slightly exothermic, raising the temperature to 51° C. The final portion of sorbitol (32 g) was added for a total of 0.638 moles followed by a final portion of acrylonitrile (190 ml) over 2.5 hr while keeping the reaction temperature below 60° C. (A total of 4.41 moles of acrylonitrile was used.) The reaction solution was then heated to 50-55° C. for 4 hr. The solution was then allowed to cool to room temperature and the reaction was neutralized by addition of acetic acid (2.5 ml). Removal of the solvent under reduced pressure gave the product as a clear, viscous oil (324 g). The IR spectrum showed a peak at 2251 cm$^{-1}$, indicative of the nitrile group. A DS=5.6 was determined by LC/MS, which is rounded to 6 in CE-Sorb6.

Reaction of CE-Sorb6 with Hydroxylamine Hydrochloride

A 1000 ml three-necked round-bottomed flask was equipped with a mechanical stirrer, condenser, and addition funnel under nitrogen. CE-Sorb6 (14.77 g, 29.5 mmol) and water (200 ml) were added to the flask and stirred. In a separate 500 mL Erlenmeyer flask, hydroxylamine hydrochloride (11.47 g, 165 mmol, 5.6 eq) was dissolved in water (178 ml) and then treated with ammonium hydroxide (22.1 ml of 28% ammonia solution, 177 mmol, 6.0 eq) for a total volume of 200 ml. The hydroxylamine solution was then added in one portion directly to the mixture in the round-bottomed flask at room temperature. The stirred mixture was heated at 80° C. for 2 hr, pH=8-9, and then allowed to cool to room temperature. The IR spectrum indicated loss of most of the nitrile peak at 2250 cm$^{-1}$ and the appearance of a new peak at 1660 cm$^{-1}$, indicative of the amidoxime of CE-Sorb6.

Example 1

Ammoniacal Solution of
Styrene/N-Hydroxymaleamic Acid Copolymer and
Copper/Tungstate Complex as Preservative A) Preparation of Styrene/N-Hydroxymaleamic Acid Copolymer and Copper/Tungstate Complex in Ammoniacal Solution A 5 L round-bottomed flask equipped with addition funnel, heating mantel, thermocouple well, and mechanical stirrer was charged with 86 g (0.425 mol) of SMA resin (prepared as described in General Methods) and 500 ml of water. A solution of 30 g hydroxylamine 50% w/w in water (0.45 mol) and 22.7 g sodium carbonate (0.21 mol) in 120 ml of water was added through the addition funnel during 20 minutes. The mixture was heated for 4 hours at 55° C. to give a clear solution. To the polymer solution was added 50 g of conc. ammonium hydroxide and 116.7 g (0.468 mol) of copper sulfate pentahydrate. A solution of 13.3 g (0.0403 mol) of sodium tungstate dihydrate dissolved in 200 g of water and 150 g of conc. ammonium hydroxide was then added. The concentrated wood treatment mixture was transferred to a jar and the remaining mixture washed into the jar by a solution of 150 g of water and 50 g of conc. ammonium hydroxide (57.6% ammonium hydroxide). The entire procedure was repeated. The products were combined and diluted with water to a final weight of 40 Kg to give an imbibing solution containing 1485 ppm copper and 500 ppm tungstate ion.

B) Penetration of Ammoniacal Solution of Styrene/N-Hydroxymaleamic Acid Copolymer and Copper/Tungstate Complex in Wood Blocks The ammoniacal solution of styrene/N-hydroxymaleamic acid copolymer and copper/tungstate complex prepared as described in Example 1A was imbibed into wood using a wood impregnation system similar to that described by the American Wood Preservers Association (AWPA) as AWPA Standard, Method E11-97. Standard laboratory glassware and a vacuum pump were used to imbibe 32 pre-weighed Southern Yellow Pine (SYP) wood blocks measuring ¾"× ¾"×¾" (19 mm×19 mm×19 mm). The blocks were free of knots, resin and sap pockets, had no visible sign of infection by mold, stain, and wood destroying fungi, had no cracks, had a ring count of 6-10 rings per inch, and contained at least 50% summer wood. The blocks were pre-conditioned for 21 days in a humidity chamber set at 23° C.+/−0.5° C. and relative humidity of 50%+/−2%. Under these conditions the blocks achieved equilibrium moisture content of 9-10%, which was determined by using a Moisture Meter, Model PM6304 from the Control Company (Friendswood, Tex.). An imbibing vessel was prepared using a glass flask measuring 10.16 cm in diam.×30.48 cm long having three openings, two of which were standard taper ground glass 29/26 joints and a central one having a standard taper ground glass 102/75 ball joint. An addition funnel was placed on one of the 29/26 joints and filled with the treatment solution. The wood cubes were placed in the imbibing vessel in a Nylon bag that was weighted with stainless steel nuts to prevent floating and the imbibing vessel was evacuated for 30 min. The vacuum was broken by introduction of 800 ml of imbibing solution. This amount of solution is sufficient to cover the blocks. Thirty-two blocks were imbibed with the solution prepared in Example 1. The blocks were imbibed under atmospheric pressure for 30 minutes. The blocks were gently wiped with a towel to remove any surface solution and were then immediately weighed while wet to ensure that the wood was penetrated by the imbibing solution. Table 1, including gross retention calculations, shows that the blocks gained weight, which indicated that the ammoniacal solution of styrene/N-hydroxymaleamic acid copolymer and copper/tungstate complex was successfully imbibed into the wood.

TABLE 1

Solution retention in wood blocks treated with ammoniacal solution of styrene/N-hydroxymaleamic acid copolymer and copper/tungstate complex.

| ID# | Dry wt (g) | Wet wt (g) | Gross retention (g) | |
|---|---|---|---|---|
| E2000130.00159A1 | 3.6172 | 8.3255 | 4.7083 | |
| E2000130.00159A2 | 4.0240 | 8.8761 | 4.8521 | |
| E2000130.00159A3 | 3.6686 | 8.4899 | 4.8213 | |
| E2000130.00159A5 | 3.7532 | 8.5476 | 4.7944 | * |
| E2000130.00159A7 | 3.7854 | 8.6708 | 4.8854 | |
| E2000130.00159A9 | 3.8787 | 8.6286 | 4.7499 | * |
| E2000130.00159A10 | 3.5361 | 8.3672 | 4.8311 | |
| E2000130.00159A11 | 4.0064 | 8.5428 | 4.5364 | |
| E2000130.00159A12 | 4.0874 | 8.9178 | 4.8304 | |
| E2000130.00159A14 | 3.7062 | 8.4062 | 4.7000 | * |
| E2000130.00159A15 | 3.7820 | 8.5746 | 4.7926 | * |
| E2000130.00159A16 | 3.8718 | 8.7471 | 4.8753 | |
| E2000130.00159A17 | 3.6558 | 8.3641 | 4.7083 | |
| E2000130.00159A18 | 3.8834 | 8.6641 | 4.7807 | * |
| E2000130.00159A19 | 3.8691 | 8.7287 | 4.8596 | |
| E2000130.00159A20 | 3.8704 | 8.7759 | 4.9055 | |
| E2000130.00159A22 | 3.8425 | 8.6851 | 4.8426 | |
| E2000130.00159A23 | 4.0303 | 8.7897 | 4.7594 | |
| E2000130.00159A24 | 3.7937 | 8.5156 | 4.7219 | * |
| E2000130.00159A26 | 4.0036 | 8.4523 | 4.4487 | |
| E2000130.00159A27 | 3.9375 | 8.7295 | 4.7920 | |
| E2000130.00159A30 | 3.9412 | 8.5578 | 4.6166 | |
| E2000130.00159A32 | 4.0361 | 8.6398 | 4.6037 | |
| | 88.5806 | | 109.4162 | |

*marks blocks having a gross retention falling within +/−5% of the group average The blocks were then dried at room temperature for 2 weeks, and were again conditioned for 21 days in a humidity chamber set at 23° C.+/−0.5° C. and relative humidity of 50%+/−2%. From the 32 SYP blocks treated as described above, six blocks having a gross retention falling within +/−5% of the group average were chosen. These blocks were chosen from those marked with an asterisk in Column 5 of Table 1 and are listed in Table 2. The total uptake of imbibing solution for these six blocks was 28.5395 g (see Table 2).

TABLE 2

Weights of SYP wood blocks at different stages of treatment.

| ID# | Dry wt (g) | Wet wt (g) | Gross retention (g) | Wt after leach test (g) |
|---|---|---|---|---|
| E2000130.00159A5 | 3.7532 | 8.5476 | 4.7944 | 3.6275 |
| E2000130.00159A9 | 3.8787 | 8.6286 | 4.7499 | 3.7632 |
| E2000130.00159A14 | 3.7062 | 8.4062 | 4.7000 | 3.5555 |
| E2000130.00159A15 | 3.7820 | 8.5746 | 4.7926 | 3.6664 |
| E2000130.00159A18 | 3.8834 | 8.6641 | 4.7807 | 3.7726 |
| E2000130.00159A24 | 3.7937 | 8.5156 | 4.7219 | 3.6496 |
| Totals | 22.79720 | 51.3367 | 28.5395 | 22.0348 |

The amount of active ingredient contained in the six wood blocks was calculated based on the weight of treatment solution contained and the weight fraction of active ingredient in the treatment solution. The concentration of copper in the imbibing solution was 1485 ppm. Therefore, the total amount of copper in the six blocks was (28.5395 g) (1485 ppm)/1,000,000=0.04238 g copper. The total amount of tungstate ion in the six blocks was (28.5395 g)(500 ppm)/1,000,000=0.01427 g.

C) Retention of Ammoniacal Solution of Styrene/N-Hydroxymaleamic Acid Copolymer and Copper/Tungstate Complex in Wood Blocks The six selected blocks prepared as above were reintroduced into the imbibing vessel, which was evacuated for 30 minutes, and 150 ml of deionized water was added to break the vacuum. The submerged blocks were imbibed with water for 30 minutes at atmospheric pressure. The remainder of the water imbibing solution was transferred to a measuring cylinder and the volume brought to 300 ml with deionized water. The blocks and water were transferred to a jar and the jar was covered. The leaching jars were agitated at 23° C.+/−0.5° C. at 100 oscillations/min on an Innova 2300 Platform Shaker table (New Brunswick Scientific Co., Inc., Edison, N.J.). The water from each jar was collected as a leachate solution and replaced with 300 ml of fresh deionized water at the following hourly intervals: 6, 24, 48, 96, 144, 192, 240, 288, 336, and 384 hours. The individual leachate solutions were analyzed for copper content by the following procedure: The leachate sample was evaporated to dryness in a jar using an oven set at 95° C. Then 1 g of sulfamic acid and 50 ml of deionized water was added and the jar was heated to 100° C. for 30 minutes. The jar was cooled to room temperature and then 6 g of aluminum sulfate octadecahydrate was added. A 15% sodium carbonate solution was used to bring the pH to neutral, followed by addition of about one to three ml of glacial acetic acid to bring the pH to approximately 4. Then 7 g of NaI was added to the room temperature solution. The solution was titrated with 0.00990 M sodium thiosulfate solution. When the solution appeared to be straw-colored, a few drops of a freshly prepared solution of 1 g of soluble starch in 100 ml of water was added, followed by addition of 1 g of potassium thiocyanate. The solution was then titrated with 0.00990 M sodium thiosulfate solution to the discharge of the blue starch/iodide color. The amount of copper present in each sample of leachate was calculated by the equation:

g Cu=(ml 0.00990 N sodium thiosulfate)(0.00990 equiv./1000 ml)(63.546 g Cu/equiv.).

From the titration of the leachate collected at each time given above, the total amount of copper remaining in the six blocks was computed as the difference between the amount determined by titration of the leach solution and the value for the previous time point. The amount of copper remaining in the six block sample at each time point is shown in Table 3.

TABLE 3

Leaching of Copper from SYP wood blocks

| Hours | Cu left in blocks (g) | Thiosulfate (ml) | Cu in soln (g) |
|---|---|---|---|
| 0 | 0.04238 | 0 | 0 |
| 6 | 0.04132 | 1.69 | 0.001063 |
| 24 | 0.04089 | 0.69 | 0.000434 |
| 48 | 0.04065 | 0.39 | 0.000245 |
| 96 | 0.04056 | 0.14 | 0.000088 |
| 144 | 0.04047 | 0.14 | 0.000088 |
| 192 | 0.04041 | 0.1 | 0.000063 |
| 240 | 0.04035 | 0.09 | 0.000057 |
| 288 | 0.0403 | 0.08 | 0.00005 |
| 336 | 0.04024 | 0.09 | 0.000057 |
| 384 | 0.040202 | 0.06 | 0.000038 |
| Total | | 3.47 | 0.002183 |

Six untreated control blocks were treated and leached as above and titrated with 0.00937 N thiosulfate to yield 0.000178 g of leachable copper background. This amount of copper was subtracted from the total amount of copper that was leached from the treated blocks (0.2183 g, Table 3) to give 0.002005 g of copper leached from the preservative. The amount of copper initially imbibed into the wood was 0.04238 g. Therefore only about 4.73% [(0.002005/0.04238) (100)] of the copper leached out of the wood under these vigorous leaching conditions. This result shows that there is excellent retention of copper in the wood when it is complexed with tungstate and styrene/N-hydroxymaleamic acid copolymer.

D) Preparation and Environmental Testing of Fahlstrom Stakes Treated with Ammoniacal Solution of Styrene/N-Hydroxymaleamic Acid Copolymer and Copper/Tungstate Complex Selection and Preparation of Fahlstrom Stakes The following methods are based on AWPA Standard, Method E7-01, Sec. 4, 5, 6, and 7 and E11-97.

SYP boards, 3.175 cm×35.56 cm×243.84 cm (5/4"×14"×8 ft) and 3.175 cm×30.48 cm×243.84 cm (5/4"×12"×8 ft) were obtained from Delaware County Supply (Boothwin, Pa.). The boards were cut into Fahlstrom stakes of 4 mm×38 mm×254 cm (0.156"×1.5"×10") in size (AWPA Standard, Method E7-01, Sec 4.2, with the exception that the boards were milled without equilibration). The stakes were segregated by visual inspection (AWPA Standard, Method E7-01, Sec. 4.1) and stakes having knots, cracks, resin and sap pockets, signs of infection by mold, stain, and wood destroying fungi were eliminated. The remaining stakes were sorted into groups by weight (AWPA Standard, Method E7-01, Sec. 5). Stakes weighing between 20 g and 25 g were chosen for the imbibing experiment and placed in a controlled environment chamber at 23° C. and RH of 50% (Model 1-60LLVL Humidity Cabinet, Percival Scientific Inc., Boone, Iowa) for 21 days (AWPA Standard, Method E7-01, Sec. 4 and E11-97, Sec. 3). After equilibration in the environment chamber, each stake was identified by a painted number. Each stake was then weighed and dimensioned and the results recorded.

Treatment of the Fahlstrom stakes was carried out in a stainless steel pressure vessel designed and fabricated at the DuPont Experimental Station (Wilmington, Del.). Pressure was supplied by a Diaphragm Pump (Model S216J10; Sprague Products Div. of Curtiss-Wright Flow Control Corp., Brecksville, Ohio). The pressure vessel was constructed from sched. 80 SS pipe measuring 12.7 cm (5") diam. and was closed at each end with SS flanges and caps. The length of the pipe varied depending on the length of the wood to be treated. Typically, a 101.6 cm (40") pipe length was chosen for treating 38" wood specimens. Other lengths of pipe were added via flanges to extend the length of the pressure vessel to accommodate 243.84 cm (8 ft) specimens or shorter lengths of pipe were used to treat 25.4 cm (10") specimens.

Batches of ten labeled stakes were loaded into a stainless steel separation rack (to simulate sticking, which is physical separation of lumber by placing small pieces of wood between boards to separate them), as well as two witness stakes (total 12 stakes), and placed in the pressure vessel. The pressure vessel was sealed and a vacuum of 69.85 cm Hg gauge (13.5 psig) was applied for a period of 30 minutes. The vacuum was broken by introduction of the imbibing fluid, the ammoniacal solution of styrene/N-hydroxymaleamic acid copolymer and copper/tungstate complex prepared in Example 1A, to fill the pressure vessel and cover the wood. Air pockets were removed by circulating imbibing fluid through the vessel, and pressure of 7.18 kilopascal gauge (150 psig) was applied with a diaphragm pump for a period of 30 minutes. The pressure was released and the stakes allowed to equilibrate in the imbibing solution for 15 minutes. The pressure vessel was drained and the treatment rack bearing the stakes was removed. The stakes were lightly wiped with a paper towel and weighed. The results given in Table 4 show that the blocks gained weight, which indicated that the ammoniacal solution of styrene/N-hydroxymaleamic acid copolymer and copper/tungstate complex was successfully imbibed into the wood.

TABLE 4

Retention of Treatment Solution in SYP Fahlstrom Stakes

| Stake ID | Dry wt (g) | Wet wt (g) | Gross Retention (g) |
|---|---|---|---|
| 159-1 | 22.66 | 46.80 | 25.14 |
| 159-2 | 24.32 | 49.82 | 25.50 |
| 159-3 | 24.02 | 49.23 | 25.21 |
| 159-4 | 23.63 | 46.75 | 23.12 |
| 159-5 | 23.67 | 48.82 | 25.15 |
| 159-6 | 22.03 | 47.36 | 25.33 |
| 159-7 | 23.77 | 48.14 | 24.37 |
| 159-8 | 24.52 | 48.77 | 24.25 |
| 159-9 | 23.87 | 49.38 | 25.51 |
| 159-10 | 24.31 | 49.80 | 25.49 |
| 159-11 | 22.49 | 47.35 | 24.86 |

TABLE 4-continued

Retention of Treatment Solution in SYP Fahlstrom Stakes

| Stake ID | Dry wt (g) | Wet wt (g) | Gross Retention (g) |
|---|---|---|---|
| 159-12 | 22.45 | 47.94 | 25.49 |
| 159-13 | 22.53 | 47.41 | 24.88 |
| 159-14 | 22.24 | 47.39 | 25.15 |
| 159-15 | 23.47 | 48.74 | 25.27 |
| 159-16 | 23.83 | 48.71 | 24.88 |
| 159-17 | 24.03 | 49.03 | 25.00 |
| 159-18 | 22.17 | 46.78 | 24.61 |
| 159-9 | 23.21 | 49.12 | 25.91 |
| 159-20 | 22.34 | 46.99 | 24.65 |
| 159-21 | 23.70 | 48.84 | 25.14 |
| 159-22 | 24.36 | 49.13 | 24.77 |
| 159-23 | 24.16 | 49.36 | 25.20 |
| 159-24 | 22.41 | 46.98 | 24.57 |
| 159-25 | 24.10 | 49.44 | 25.34 |
| 159-26 | 24.06 | 49.36 | 25.30 |
| 159-27 | 24.17 | 48.84 | 24.67 |
| 159-28 | 24.27 | 48.22 | 23.95 |
| 159-29 | 23.91 | 48.84 | 24.93 |
| 159-30 | 22.36 | 48.83 | 26.47 |
| 159-31 | 23.60 | 45.64 | 22.04 |
| 159-32 | 22.63 | 44.09 | 21.46 |
| 159-33 | 23.93 | 45.37 | 21.44 |
| 159-34 | 24.09 | 43.67 | 19.58 |
| 159-35 | 24.37 | 46.55 | 22.18 |
| 159-36 | 23.96 | 44.42 | 20.46 |
| 159-37 | 24.08 | 47.76 | 23.68 |
| 159-38 | 23.06 | 47.61 | 24.55 |
| 159-39 | 24.19 | 49.13 | 24.94 |
| 159-40 | 24.02 | 48.81 | 24.79 |
| 159-41 | 23.65 | 48.89 | 25.24 |
| 159-42 | 23.04 | 48.28 | 25.24 |
| 159-43 | 22.46 | 49.52 | 27.06 |
| 159-44 | 23.69 | 48.47 | 24.78 |

Environmental Testing of Treated Wood Fahlstrom Stakes

The Fahlstrom stakes described above were placed in the ground, as per AWPA E7-01, in Hialeah, Fla. In addition, untreated control stakes were placed in the ground. The positioning of the stakes was randomized in the test sites as per AWPA E7-01. After 3, 8, 14, and 20 months, the stakes were removed from the ground and visually graded for rot (decay) according to AWPA protocol E7-01. After each evaluation, the stakes were returned to their original hole and position as per AWPA E7-01. The grades for each treated stake, along with untreated controls, were recorded and are given in Table 5. At 20 months the average score for the ten treated Fahlstrom stakes was 9.5, while the average score for ten untreated control stakes was 2.9.

TABLE 5

Decay gradings of Fahlstrom stakes treated with ammoniacal solution of styrene/N-hydroxymaleamic acid copolymer (SMA-NOH) and copper/tungstate complex (Cu/WO$_4$) of Example 1A, and tested in Hialeah, FL.

| | | Grading date/experimental time point/score | | | |
|---|---|---|---|---|---|
| Installed Jun. 15, 2004 Treatment | Stake ID | Sep. 21, 2004 3 mo | Feb. 15, 2005 8 mo | Aug. 17, 2005 14 mo | Feb. 2, 2006 20 mo |
| 1485 ppm Cu/500 ppm WO$_4$/SMA-NOH | 159-05 | 9 | 10 | 10 | 10 |
| | 159-17 | 10 | 10 | 10 | 10 |
| | 159-19 | 10 | 9 | 10 | 10 |
| | 159-21 | 10 | 10 | 9 | 9 |
| | 159-23 | 10 | 10 | 10 | 9 |
| | 159-28 | 10 | 10 | 10 | 9 |

TABLE 5-continued

Decay gradings of Fahlstrom stakes treated with
ammoniacal solution of styrene/N-hydroxymaleamic acid
copolymer (SMA-NOH) and copper/tungstate complex
(Cu/WO$_4$) of Example 1A, and tested in Hialeah, FL.

| | | Grading date/experimental time point/score | | | |
|---|---|---|---|---|---|
| Installed Jun. 15, 2004 | | Sep. 21, 2004 | Feb. 15, 2005 | Aug. 17, 2005 | Feb. 2, 2006 |
| Treatment | Stake ID | 3 mo | 8 mo | 14 mo | 20 mo |
| | 159-34 | 10 | 10 | 10 | 9 |
| | 159-39 | 10 | 10 | 10 | 10 |
| | 159-41 | 10 | 10 | 10 | 9 |
| | 159-42 | 10 | 10 | 10 | 10 |
| | Avg. | 9.9 | 9.9 | 9.9 | 9.5 |
| | SD | 0.3 | 0.3 | 0.32 | 0.5 |
| Untreated Controls | 170-11 | 7 | 6 | 0 | 0 |
| | 170-12 | 7 | 6 | 0 | 0 |
| | 170-13 | 10 | 10 | 8 | 6 |
| | 170-14 | 8 | 6 | 0 | 0 |
| | 170-15 | 9 | 10 | 9 | 8 |
| | 170-16 | 10 | 9 | 8 | 8 |
| | 170-17 | 7 | 4 | 0 | 0 |
| | 170-18 | 8 | 8 | 8 | 7 |
| | 170-19 | 7 | 6 | 0 | 0 |
| | 170-20 | 6 | 4 | 0 | 0 |
| | Avg | 7.9 | 6.9 | 3.3 | 2.9 |
| | SD | 1.3 | 2.12 | 4.27 | 3.59 |

In a similar manner, Fahlstrom Stakes were prepared with the same treatment and environmentally tested at three additional sites. A summary of the results are given in Table 6 as averages of gradings at each site, including the Hialeah site.

TABLE 6

Averages of gradings of Fahlstrom stakes treated with
ammoniacal solution of 1485 ppm Cu/500 ppm WO$_4$/SMA-NOH
(prepared in Example 1A) and tested at different sites.

| | | Treatment | | | |
|---|---|---|---|---|---|
| | | 1485 Cu/500 WO$_4$/SMA-NOH | | None - Control | |
| Location | Time (Months) | Avg Decay | Avg Insect damage | Avg Decay | Avg Insect damage |
| Hialeah, FL | 20 months | 9.5 | xxx | 2.9 | xxx |
| LaPlace, LA | 21 months | 9.1 | 9.75 | 2.85 | 3.7 |
| Starke, FL | 18 months | 9.9 | 10 | 4.8 | 4.4 |
| Newark, DE | 21 months | 9.8 | 10 | 6 | 8.4 | xxx means no insect attack observed at that site.

In the testing periods at all sites, the treated Fahlstrom stakes showed little to no decay and insect damage (where applicable) while the controls showed extensive damage.

E) Wood Preservation Treatment Procedure and Environmental Testing for Decay Stakes Pre-decay stakes were cut from SYP boards as described for the Fahlstrom stakes in Example 1D except the dimensions were 3/4"×3/4"×38" (19 mm×19 mm×1154 mm). The stakes were chosen and then imbibed as described in Example 1D. A set of stakes was imbibed with the ammoniacal solution of styrene/N-hydroxymaleamic acid copolymer and copper/tungstate complex prepared as described in Example 1A, containing 1485 ppm copper and 500 ppm tungstate ion. Additional sets of stakes were imbibed with a 1:2 dilution of the initial solution, containing 743 ppm copper and 250 ppm tungstate ion, and a 1:4 dilution, containing 372 ppm copper and 125 ppm tungstate ion. Dilutions were made with a 1.4% ammonia water solution. The stakes were placed on open racks in a ventilated enclosure to dry.

The labeled pre-decay stakes were cut into decay stakes that were 45.7 cm (18") in length, cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Each 45.7 cm (18") stake was weighed, dimensioned and the results recorded. The group of 10 stakes from each half were bundled together and labeled for ground insertion at two separate test sites (Newark, Del. and Starke, Fla.). The bundles were stored in a cool area (AWPA Standard, Method E7-01, Sec. 7) until the stakes were installed in the ground. The stakes were placed in the ground as per AWPA E7-01, along with untreated control stakes. The positioning of the stakes was randomized in the test sites as per AWPA E7-01. After 12 months the stakes in Starke, Fla. were removed from the ground and visually graded for decay and termite attack according to AWPA protocol E7-01. The results given in Table 7 show that stakes treated with any of the three test solutions had much less fungal decay and insect attack damage than untreated control stakes. The undiluted solution provided the most resistance to decay and insect damage.

TABLE 7

Decay and insect damage data for decay stakes
treated with different dilutions of 1485 ppm Cu/500 ppm
WO$_4$/SMA-NOH preservative solution (prepared in
Example 1A) and tested in Starke, FL.

| | | 12 mo grading/score | |
|---|---|---|---|
| Treatment | Stake ID | Decay | Insect damage |
| 00179 | F1438 | 10 | 10 |
| 1485 ppm Cu/500 ppm WO$_4$/SMA-NOH | F1440 | 10 | 10 |
| | F1442 | 10 | 10 |
| | F1444 | 10 | 10 |
| | F1446 | 10 | 10 |

TABLE 7-continued

Decay and insect damage data for decay stakes treated with different dilutions of 1485 ppm Cu/500 ppm WO$_4$/SMA-NOH preservative solution (prepared in Example 1A) and tested in Starke, FL.

| Treatment | Stake ID | 12 mo grading/score | |
|---|---|---|---|
| | | Decay | Insect damage |
| | F1448 | 10 | 10 |
| | F1450 | 10 | 10 |
| | F1452 | 10 | 10 |
| | F1454 | 10 | 10 |
| | F1456 | 10 | 10 |
| | Avg | 10 | 10 |
| | SD | 0 | 0 |
| 00180 | F1508 | 10 | 10 |
| 743 ppm Cu/250 ppm WO$_4$ | F1510 | 10 | 10 |
| 250/SMA-NOH | F1512 | 10 | 10 |
| | F1514 | 10 | 10 |
| | F1516 | 10 | 7 |
| | F1516 | 10 | 10 |
| | F1518 | 10 | 10 |
| | F1520 | 8 | 7 |
| | F1522 | 10 | 10 |
| | F1524 | 10 | 10 |
| | Avg | 9.8 | 9.4 |
| | SD | 0.6 | 1.2 |
| 00181 | F1526 | 10 | 10 |
| 372 ppm Cu/125 ppm WO$_4$/SMA-NOH | F1528 | 8 | 10 |
| | F1530 | 9 | 8 |
| | F1532 | 10 | 10 |
| | F1534 | 10 | 10 |
| | F1536 | 10 | 10 |
| | F1538 | 10 | 9 |
| | F1540 | 9 | 10 |
| | F1542 | 6 | 9 |
| | F1544 | 10 | 10 |
| | Avg | 9.2 | 9.6 |
| | SD | 1.25 | 0.66 |
| Untreated Controls | 1440 | 0 | 0 |
| | 1442 | 8 | 6 |
| | 1444 | 0 | 0 |
| | 1446 | 6 | 6 |
| | 1448 | 6 | 6 |
| | 1450 | 6 | 4 |
| | 1452 | 6 | 6 |
| | 1454 | 6 | 4 |
| | 1456 | 0 | 0 |
| | 1458 | 6 | 6 |
| | Avg | 4.4 | 3.8 |
| | SD | 2.94 | 2.6 |

Results of environmental testing at Newark, Del. is given in summary form as averages of gradings, along with the averages of the Starke data from Table 7, in Table 8.

TABLE 8

Averages of decay and insect damage data for decay stakes treated with different dilutions of 1485 ppm Cu/500 ppm WO$_4$/SMA-NOH preservative solution (prepared in Example 1A) and tested in Newark, DE and Starke, FL.

| Location | Conc. (PPM) | Time (Months) | Avg. Decay | Avg. Insect damage |
|---|---|---|---|---|
| Starke, FL | Cu 1485/WO4 500/ SMA-NOH | 12 | 10 | 10 |
| Starke, FL | Cu 743/WO4 250/ SMA-NOH | 12 | 9.8 | 9.4 |
| Starke, FL | Cu 371/WO4 125/ SMA-NOH | 12 | 9.2 | 9.6 |
| Starke, FL | Control | 12 | 4.4 | 3.8 |
| Newark, DE | Cu 1485/WO4 500/ SMA-NOH | 12 | 10 | 10 |
| Newark, DE | Cu 743/WO4 250/ SMA-NOH | 12 | 10 | 10 |
| Newark, DE | Cu 371/WO4 125/ SMA-NOH | 12 | 10 | 10 |
| Newark, DE | Control | 12 | 9.7 | 10 |

With damage to controls extensive, strong protection by all treatment solutions was observed at the Starke, Fla. site. There was little decay and insect damage at the Newark site in 12 months due to the colder climate and lesser amount of rainfall. It is expected that over longer periods of time, treated decay stakes at the Newark site will show less decay and insect damage with respect to controls. It is to be noted that Fahlstrom stakes treated with the same undiluted solution displayed much less decay and insect damage than untreated controls at both sites (see Table 6). Fahlstrom stakes are recognized as an accelerated test for both fungal decay and insect attack.

Example 2

Ammoniacal Solution of Styrene/N-Hydroxymaleamic Acid Copolymer and Copper/Molybdate Complex as Preservative A) Preparation of Styrene/N-Hydroxymaleamic Acid Copolymer and Copper/Molybdate Complex in Ammoniacal Solution A 5 L round-bottomed flask equipped with addition funnel, heating mantel, thermocouple well, and mechanical stirrer was charged with 600 ml of tetrahydrofuran (THF). To the THF was added 121 g of commercial SMA resin (Aldrich; Milwaukee, Wis.). All of the SMA resin dissolved in 10 minutes. A solution of 27.3 g of sodium carbonate and 34.4 g of 50% aqueous hydroxylamine and 120 ml of water was prepared. This solution was added through the dropping funnel to the THF solution during 35 minutes. Then 600 ml of water was added and the whole stirred for one hour. The THF was removed by distillation to leave an aqueous solution of styrene N-hydroxymaleamic acid. To half of the solution was added a solution 29.17 g of copper sulfate pentahydrate dissolved in 100 g of water and 100 g of concentrated ammonium hydroxide, and a solution of 5.04 g of sodium molybdate dissolved in 20 g of water to prepare a concentrated wood preservative solution. The concentrate was diluted to 10 Kg with 1.4% ammonia water to prepare a wood preservative solution containing 742 ppm of copper and 333 ppm of molybdate ion.

B) Penetration of Ammoniacal Solution of Styrene/N-Hydroxymaleamic Acid Copolymer and Copper/Molybdate Complex in Wood Blocks The ammoniacal solution of styrene/N-hydroxymaleamic acid copolymer and copper/molybdate complex prepared as described in Example 2A was imbibed into wood blocks as described in Example 1. Table 9, including gross retention calculations, shows that the blocks gained weight, which indicated that the ammoniacal solution of styrene/N-hydroxymaleamic acid copolymer and copper/molybdate complex was successfully imbibed into the wood.

TABLE 9

Solution retention in wood blocks treated with ammoniacal solution of styrene/N-hydroxymaleamic acid copolymer and copper/molybdate complex.

| ID# | Dry wt (g) | Wet wt (g) | Gross retention (g) | |
|---|---|---|---|---|
| E2000130.00168A1 | 3.8991 | 9.1047 | 5.2056 | |
| E2000130.00168A2 | 4.9047 | 8.8745 | 3.9698 | |
| E2000130.00168A3 | 4.9454 | 9.1939 | 4.2485 | |
| E2000130.00168A4 | 4.9742 | 9.4768 | 4.5026 | |
| E2000130.00168A5 | 4.7385 | 8.9023 | 4.1638 | * |
| E2000130.00168A6 | 3.6493 | 8.5204 | 4.8711 | |
| E2000130.00168A7 | 4.9168 | 9.4472 | 4.5304 | |
| E2000130.00168A8 | 4.9702 | 9.5955 | 4.6253 | |
| E2000130.00168A9 | 4.6878 | 8.9616 | 4.2738 | |
| E2000130.00168A10 | 4.7813 | 9.3520 | 4.5707 | * |
| E2000130.00168A11 | 4.7413 | 8.5686 | 3.8273 | |
| E2000130.00168A12 | 4.8363 | 9.1786 | 4.3423 | * |
| E2000130.00168A13 | 4.6493 | 8.9740 | 4.3247 | |
| E2000130.00168A14 | 4.8536 | 9.0832 | 4.2296 | |
| E2000130.00168A15 | 4.8399 | 9.2587 | 4.4188 | |
| E2000130.00168A16 | 5.0658 | 9.2511 | 4.1853 | |
| E2000130.00168A17 | 4.6878 | 9.3805 | 4.6927 | |
| E2000130.00168A18 | 4.7687 | 9.3524 | 4.5837 | * |
| E2000130.00168A19 | 4.6678 | 8.8874 | 4.2196 | |
| E2000130.00168A20 | 5.0441 | 7.8434 | 2.7993 | |
| E2000130.00168A21 | 4.7376 | 9.3956 | 4.6580 | * |
| E2000130.00168A22 | 4.6473 | 8.1333 | 3.4860 | |
| E2000130.00168A23 | 3.8822 | 8.9369 | 5.0547 | |
| E2000130.00168A24 | 4.6947 | 9.0220 | 4.3273 | * |
| E2000130.00168A25 | 3.8847 | 7.7353 | 3.8506 | |
| E2000130.00168A26 | 3.5690 | 8.3760 | 4.8070 | |
| E2000130.00168A27 | 4.8004 | 8.7275 | 3.9271 | |
| E2000130.00168A28 | 5.1454 | 9.1544 | 4.0090 | |
| E2000130.00168A29 | 4.6507 | 9.1391 | 4.4884 | |
| E2000130.00168A30 | 4.7560 | 8.6243 | 3.8683 | |
| E2000130.00168A31 | 4.6689 | 9.4617 | 4.7928 | |
| E2000130.00168A32 | 3.9008 | 8.7815 | 4.8807 | |
| | 147.9596 | | 138.7348 | |

*marks blocks having a gross retention falling within +/−5% of the group average The blocks were then dried at room temperature for 2 weeks, and were again conditioned for 21 days in a humidity chamber set at 23° C.+/−0.5° C. and relative humidity of 50%+/−2%. From the 32 SYP blocks treated as above, six blocks having a gross retention falling within +/−5% of the group average were chosen. These blocks were chosen from those marked with an asterisk in Column 5 of Table 9 and are listed in Table 10. The total uptake of imbibing solution for these six blocks was 26.6458 g (see Table 10).

TABLE 10

Weights of SYP wood blocks at different stages of treatment.

| ID# | Dry wt (g) | Wet wt (g) | Gross retention (g) | Wt after leaching (g) |
|---|---|---|---|---|
| E2000130.00168A5 | 4.7385 | 8.9023 | 4.1638 | 4.5542 |
| E2000130.00168A10 | 4.7813 | 9.3520 | 4.5707 | 4.5491 |
| E2000130.00168A12 | 4.8363 | 9.1786 | 4.3423 | 4.6257 |
| E2000130.00168A18 | 4.7687 | 9.3524 | 4.5837 | 4.5557 |
| E2000130.00168A21 | 4.7376 | 9.3956 | 4.6580 | 4.5414 |
| E2000130.00168A24 | 4.6947 | 9.0220 | 4.3273 | 4.5018 |
| Totals | | | 26.6458 | 27.3279 |

The amount of active ingredient contained in the six wood blocks was calculated based on the weight of treatment solution contained and the weight fraction of active ingredient in the treatment solution. The total uptake of imbibing solution for the six blocks was 26.6458 g (see Table 10). The concentration of copper in the imbibing solution was 742 ppm. Therefore, the total amount of copper in the six blocks was (26.6458 g) (742 ppm)/1,000,000=0.0198 g copper. The total amount of molybdate in the six blocks was (26.6458 g) (333 ppm)/1,000,000=0.008873 g of molybdate ion.

C) Retention of Ammoniacal Solution of Styrene/N-Hydroxymaleamic Acid Copolymer and Copper/Molybdate Complex in Wood Blocks The six selected blocks were tested for leaching of copper as described in Example 1C. Following addition of 7 g of NaI to the room temperature solution, the solution was titrated with 0.00984 M sodium thiosulfate solution. When the solution appeared to be straw-colored, a few drops of a freshly prepared solution of 1 g of soluble starch in 100 ml of water was added followed by addition of 1 g of potassium thiocyanate. The solution was then titrated with 0.00984 M sodium thiosulfate solution to the discharge of the blue starch/iodide color. The amount of copper present in each sample of leachate was calculated by the equation:

g Cu=(ml 0.00984 N sodium thiosulfate)(0.00984 equiv./1000 ml)(63.546 g Cu/equiv.).

From the titration of the leachate collected at each time given above, the total amount of copper remaining in the six blocks was computed as the difference between the amount determined by titration of the leach solution and the value for the previous time point. The amount of copper that remained in the six block sample at each time point is shown in Table 11.

TABLE 11

Leaching of Copper from SYP wood blocks

| Hours | Cu left in blocks (g) | Thiosulfate (ml) | Cu in soln (g) |
|---|---|---|---|
| 0 | 0.019785 | 0 | 0 |
| 6 | 0.019197 | 0.94 | 0.000588 |
| 24 | 0.018872 | 0.52 | 0.000325 |
| 48 | 0.018728 | 0.23 | 0.000144 |
| 96 | 0.018609 | 0.19 | 0.000119 |
| 144 | 0.018553 | 0.09 | 0.000056 |
| 192 | 0.018522 | 0.05 | 0.000031 |
| 240 | 0.018491 | 0.05 | 0.000031 |
| 288 | 0.018466 | 0.04 | 0.000025 |
| 336 | 0.018447 | 0.03 | 0.000019 |
| 384 | 0.018434 | 0.02 | 0.000013 |
| Totals | | 2.16 | 0.001351 |

Six untreated control blocks were treated and leached as above and titrated with 0.00937 N thiosulfate to yield 0.000178 g of leachable copper background. This amount of copper was subtracted from the total amount of copper that was leached from the treated blocks (0.001351 g, Table 11 to give 0.001173 g of copper leached from the preservative. The amount of copper initially imbibed into the wood was 0.0198 g. Therefore only about 5.92%=[(0.001173/0.0198)(100)] of the copper leached out of the wood under these vigorous leaching conditions. This result shows that there is excellent retention of copper in the wood when it is introduced as an ammoniacal solution of styrene/N-hydroxymaleamic acid copolymer and copper/molybdate complex.

D) Preparation and Environmental Testing of Stakes Treated with Ammoniacal Solution of Styrene/N-Hydroxymaleamic Acid Co-Polymer and Copper/Molybdate Complex Forty-four Fahlstrom stakes were prepared and treated with the solution prepared in Example 2A as described in Example 1D. The results given in Table 12 show that the blocks gained weight, which indicated that the ammoniacal solution of styrene/N-hydroxymaleamic acid copolymer and copper/tungstate complex was successfully imbibed into the wood.

TABLE 12

Retention of Treatment Solution in SYP Fahlstrom Stakes

| Stake ID | Dry Wt. (g) | Wet Wt. (g) | Gross Retention (g) |
|---|---|---|---|
| 168-1 | 20.2 | 39.47 | 19.27 |
| 168-2 | 22.52 | 42.24 | 19.72 |
| 168-3 | 15.57 | 42.69 | 27.12 |
| 168-4 | 23.75 | 45.76 | 22.01 |
| 168-5 | 18.19 | 41.13 | 22.94 |
| 168-6 | 24.66 | 48.63 | 23.97 |
| 168-7 | 25.21 | 47.08 | 21.87 |
| 168-8 | 18.75 | 44.73 | 25.98 |
| 168-9 | 25.77 | 49.01 | 23.24 |
| 168-10 | 22.57 | 47.74 | 25.17 |
| 168-11 | 21.23 | 46.65 | 25.42 |
| 168-12 | 23.09 | 47.76 | 24.67 |
| 168-13 | 23.4 | 47.61 | 24.21 |
| 168-14 | 25.54 | 48.89 | 23.35 |
| 168-15 | 21.74 | 45.47 | 23.73 |
| 168-16 | 21.8 | 44.68 | 22.88 |
| 168-17 | 18.83 | 41.01 | 22.18 |
| 168-18 | 21.51 | 38.3 | 16.79 |
| 168-19 | 15.58 | 44.99 | 29.41 |
| 168-20 | 22.38 | 45.58 | 23.2 |

TABLE 12-continued

Retention of Treatment Solution in SYP Fahlstrom Stakes

| Stake ID | Dry Wt. (g) | Wet Wt. (g) | Gross Retention (g) |
|---|---|---|---|
| 168-21 | 25.75 | 48.43 | 22.68 |
| 168-22 | 22.24 | 48.75 | 26.51 |
| 168-23 | 26.5 | 50.95 | 24.45 |
| 168-24 | 21.38 | 47.55 | 26.17 |
| 168-25 | 25.19 | 50.08 | 24.89 |
| 168-26 | 22.25 | 47.4 | 25.15 |
| 168-27 | 21.27 | 45.2 | 23.93 |
| 168-28 | 21.18 | 44.27 | 23.09 |
| 168-29 | 24.7 | 50.64 | 25.94 |
| 168-30 | 19.45 | 45.47 | 26.02 |
| 168-31 | 21.32 | 46.71 | 25.39 |
| 168-32 | 22.13 | 47.82 | 25.69 |
| 168-33 | 21.96 | 47.83 | 25.87 |
| 168-34 | 25.96 | 49.93 | 23.97 |
| 168-35 | 18.05 | 45.7 | 27.65 |
| 168-36 | 23.37 | 48.48 | 25.11 |
| 168-37 | 24.59 | 48.19 | 23.6 |
| 168-38 | 24.01 | 47.81 | 23.8 |
| 168-39 | 24.49 | 46.86 | 22.37 |
| 168-40 | 26.14 | 48 | 21.81 |
| 168-41 | 21.22 | 46.48 | 25.26 |
| 168-42 | 14.38 | 44.4 | 30.02 |
| 168-43 | 16.76 | 41.27 | 24.51 |
| 168-44 | 20.15 | 20.15 | 20.15 |

The stakes were environmentally tested also as described in Example 1D. Stakes put in the ground in Hialeah, Fla. were evaluated for decay after 9, 14, 20, 26 and 32 months and results are given in Table 13. The average score for the ten treated stakes was 8.0 after 32 months of burial, while the average score for ten untreated control stakes was 1.6.

TABLE 13

Decay gradings of Fahlstrom stakes treated with ammoniacal solution of styrene/N-hydroxymaleamic acid copolymer and copper/molybdate complex (of Example 2A), tested in Hialeah, FL.

| Installed | | Grading date/experimental time point/score | | | | |
|---|---|---|---|---|---|---|
| Dec. 10, 2003 Treatment | Stake ID | Sep. 21, 2004 9 mo | Feb. 15, 2005 14 mo | Aug. 17, 2005 20 mo | Feb. 2, 2006 26 mo | Aug. 1, 2006 32 mo |
| 742 ppm Cu/333 ppm MoO$_4$/SMA-NOH | 168-10 | 10 | 10 | 10 | 10 | 8 |
| | 168-14 | 10 | 10 | 9 | 9 | 7 |
| | 168-16 | 10 | 10 | 9 | 9 | 8 |
| | 168-20 | 10 | 10 | 10 | 9 | 9 |
| | 168-23 | 10 | 10 | 9 | 9 | 7 |
| | 168-24 | 10 | 10 | 10 | 10 | 10 |
| | 168-31 | 10 | 10 | 10 | 10 | 7 |
| | 168-38 | 10 | 10 | 9 | 9 | 8 |
| | 168-40 | 10 | 10 | 9 | 9 | 8 |
| | 168-43 | 10 | 10 | 10 | 10 | 8 |
| | Avg | 10 | 10 | 9.5 | 9.4 | 8.0 |
| | SD | 0 | 0 | 0.53 | 0.49 | 0.89 |
| Untreated Controls | 170-11 | 7 | 6 | 0 | 0 | 0 |
| | 170-12 | 7 | 6 | 0 | 0 | 0 |
| | 170-13 | 10 | 10 | 8 | 6 | 0 |
| | 170-14 | 8 | 6 | 0 | 0 | 0 |
| | 170-15 | 9 | 10 | 9 | 8 | 6 |
| | 170-16 | 10 | 9 | 8 | 8 | 4 |
| | 170-17 | 7 | 4 | 0 | 0 | 0 |
| | 170-18 | 8 | 8 | 8 | 7 | 6 |
| | 170-19 | 7 | 6 | 0 | 0 | 0 |
| | 170-20 | 6 | 4 | 0 | 0 | 0 |
| | Avg | 7.9 | 6.9 | 3.3 | 2.9 | 1.6 |
| | SD | 1.3 | 2.12 | 4.27 | 3.59 | 2.50 |

In a similar manner, Fahlstrom Stakes were prepared with the same treatment and environmentally tested at three additional sites. A summary of the results are given in Table 14 as averages of gradings at each site, including the Hialeah site.

TABLE 14

Averages of gradings of Fahlstrom stakes treated with 742 ppm Cu/333 ppm MoO$_4$/SMA-NOH (prepared in Example 2A) and tested at different sites.

| | | Treatment | | | |
|---|---|---|---|---|---|
| | | 742 Cu/333 MoO$_4$/SMA-NOH | | None - Control | |
| Location | Time (Months) | Avg. Decay | Avg Insect damage | Avg Decay | Avg Insect damage |
| Hialeah, FL | 32 | 8 | xxx | 1.6 | xxx |
| LaPlace, LA | 27 | 8.05 | 9 | 1.7 | 2.35 |
| Starke, FL | 18 | 9.5 | 9.8 | 4.8 | 4.4 |
| Newark, DE | 21 | 9.35 | 9.8 | 6 | 8.4 | xxx means no insect attack observed at that site.

A preservative solution similar to the one used to prepare Fahlstrom stakes but containing twice the amounts of ingredients, i.e., 1485 ppm copper and 666 ppm molybdate ion in an ammoniacal solution of styrene/N-hydroxymaleamic acid co-polymer was prepared and used to pressure treat Decay Stakes as described in 1E. A set of stakes was imbibed with the full strength solution, containing 1485 ppm copper and 666 ppm molybdate ion. Additional sets of stakes were imbibed with 1:2 and 1:4 dilutions of the initial solution, diluted with 1.4% ammonia water. The stakes were placed in the ground at Starke, Fla. and visually graded after 12 months using AWPA E7-01 standards. The results are given in Table 15.

TABLE 15

Decay and insect damage data for stakes treated with different dilutions of ammoniacal solution of styrene/N-hydroxymaleamic acid copolymer and copper/molybdate complex tested in Starke, FL.

| | | 12 mo scores | |
|---|---|---|---|
| Treatment | Stake ID | Decay | Insect damage |
| 00185 | F1658 | 10 | 10 |
| 1485 ppm Cu/666 ppm | F1660 | 10 | 10 |
| MoO$_4$/SMA-NOH | F1662 | 10 | 10 |
| | F1664 | 10 | 10 |
| | F1666 | 10 | 10 |
| | F1668 | 10 | 10 |
| | F1670 | 10 | 10 |
| | F1672 | 10 | 10 |
| | F1674 | 10 | 10 |
| | F1676 | 10 | 10 |
| | Avg | 10 | 10 |
| | SD | 0 | 0 |
| 00186 | F1728 | 10 | 10 |
| 743 ppm C/333 ppm | F1730 | 10 | 10 |
| MoO$_4$/SMA-NOH | F1732 | 9 | 10 |
| | F1734 | 10 | 10 |
| | F1736 | 10 | 10 |
| | F1738 | 10 | 10 |
| | F1740 | 10 | 10 |
| | F1742 | 10 | 10 |
| | F1744 | 10 | 10 |
| | F1746 | 10 | 10 |
| | Avg | 9.9 | 10 |
| | SD | 0.3 | 0 |
| 00187 | F1748 | 8 | 7 |
| 371 ppm Cu/167 ppm | F1750 | 10 | 10 |
| MoO$_4$/SMA-NOH | F1752 | 10 | 10 |
| | F1754 | 10 | 10 |
| | F1756 | 9 | 8 |
| | F1758 | 10 | 10 |
| | F1760 | 10 | 10 |
| | F1762 | 10 | 10 |
| | F1764 | 10 | 10 |
| | F1766 | 10 | 9 |
| | Avg | 9.7 | 9.4 |
| | SD | 0.64 | 1.02 |
| 00196 | W0408 | 9 | 8 |
| Untreated Control Stakes | W0410 | 9 | 9 |
| | W0412 | 9 | 9 |
| | W0414 | 7 | 7 |
| | W0416 | 9 | 10 |
| | W0418 | 6 | 6 |
| | W0420 | 7 | 8 |
| | W0422 | 10 | 10 |
| | W0424 | 7 | 7 |
| | Avg | 8.1 | 8.2 |
| | SD | 1.28 | 1.31 |

The treated stakes showed less fungal decay and insect damage than the untreated control stakes.

In a similar manner, Decay Stakes were prepared with the same treatments and environmentally tested at Newark, Del. A summary of the results are given in Table 16 as averages of gradings at Newark, Del., along with averages of the data from Starke, Fla.

TABLE 16

Averages of decay and insect damage data for stakes treated with different dilutions of ammoniacal solution of styrene/N-hydroxymaleamic acid copolymer and copper/molybdate complex tested in Newark, DE or Starke, FL.

| Location | Conc. (PPM) | Time (Months) | Avg.Decay | Avg.Insect damage |
|---|---|---|---|---|
| Starke, FL | Cu(1485)MoO$_4$(666)SMA-NOH | 12 | 10 | 10 |
| | Cu(742)MoO$_4$(333)SMA-NOH | 12 | 9.9 | 10 |
| | Cu(371)MoO$_4$(167)SMA-NOH | 12 | 9.7 | 9.4 |
| | Control | 12 | 8.1 | 8.2 |

TABLE 16-continued

Averages of decay and insect damage data for stakes
treated with different dilutions of ammoniacal solution
of styrene/N-hydroxymaleamic acid copolymer and
copper/molybdate complex tested in Newark, DE or
Starke, FL.

| Location | Conc. (PPM) | Time (Months) | Avg.Decay | Avg.Insect damage |
|---|---|---|---|---|
| Newark, DE | Cu(1485)MoO$_4$(666)SMA-NOH | 12 | 10 | 10 |
| | Cu(742)MoO$_4$(333)SMA-NOH | 12 | 10 | 10 |
| | Cu(371)MoO$_4$(167)SMA-NOH | 12 | 9.9 | 10 |
| | Control | 12 | 9.7 | 10 |

With decay and insect damage in controls, protection by all treatment solutions was observed at the Starke, Fla. site. Since there was little decay and insect damage at the Newark site in 12 months, the differences between the treated and control stakes are small to none. It is expected that over longer periods of time, treated decay stakes will show less damage with respect to controls at this site.

Example 3

Ammoniacal Solution of Copper/Tungstate Complex as Preservative

A) Preparation of Copper/Tungstate Complex in Ammoniacal Solution

A solution of 58.35 g of copper sulfate pentahydrate, 77.09 g of sodium tungstate dihydrate, 86 g of concentrated ammonium hydroxide (57% ammonium hydroxide in water) and 778 g of water was prepared. To this solution was added enough water to prepare 1 Kg of concentrate The concentrate was diluted to 10 Kg with 1.4% ammonia water to prepare 10 Kg of wood treatment solution containing 1485 ppm of copper and 5792 ppm of tungstate ion.

D) Preparation and Environmental Testing of Stakes Treated with Ammoniacal Solution of Copper/Tungstate Complex Forty-four Fahlstrom stakes were prepared and treated with the solution prepared in Example 3A in batches of up to 10 stakes, as described in Example 1D. The uptake of treatment solution was evident from the results displayed in Table 17.

TABLE 17

Retention of Treatment Solution in SYP Fahlstrom Stakes

| Stake ID | Dry wt (g) | Wet wt (g) | Gross retention (g) | Dry wt 2 wk (g) |
|---|---|---|---|---|
| 144-1 | 24.16 | 47.67 | 23.51 | 23.48 |
| 144-2 | 20.23 | 46.72 | 26.49 | 19.72 |
| 144-3 | 23.48 | 47.11 | 23.63 | 22.89 |
| 144-4 | 23.57 | 47.38 | 23.81 | 22.96 |
| 144-5 | 24.65 | 49.74 | 25.09 | 24.14 |
| 144-6 | 25.32 | 48.1 | 22.78 | 24.52 |
| 144-7 | 22.88 | 47.61 | 24.73 | 22.19 |
| 144-8 | 23.85 | 49.64 | 25.79 | 23.2 |
| 144-9 | 23.55 | 49.16 | 25.61 | 22.88 |
| 144-10 | 22.21 | 48.01 | 25.8 | 21.5 |
| 144-11 | 21.55 | 47.29 | 25.74 | 20.97 |
| 144-12 | 21.43 | 45.57 | 24.14 | 20.69 |
| 144-13 | 20.13 | 43.9 | 23.77 | 19.67 |
| 144-14 | 21.88 | 48.26 | 26.38 | 21.25 |
| 144-15 | 23.41 | 48.65 | 25.24 | 22.77 |

TABLE 17-continued

Retention of Treatment Solution in SYP Fahlstrom Stakes

| Stake ID | Dry wt (g) | Wet wt (g) | Gross retention (g) | Dry wt 2 wk (g) |
|---|---|---|---|---|
| 144-16 | 24.97 | 49.08 | 24.11 | 24.27 |
| 144-17 | 21.63 | 46.81 | 25.18 | 20.94 |
| 144-18 | 23.29 | 50.41 | 27.12 | 22.67 |
| 144-19 | 20.81 | 48.83 | 28.02 | 20.19 |
| 144-20 | 22.36 | 49.26 | 26.9 | 21.96 |
| 144-21 | 22.83 | 47.13 | 24.3 | 22.13 |
| 144-22 | 20.34 | 45.09 | 24.75 | 19.72 |
| 144-23 | 23.49 | 49.03 | 25.54 | 23 |
| 144-24 | 21.98 | 48.58 | 26.6 | 21.36 |
| 144-25 | 21.54 | 49.93 | 28.39 | 21.05 |
| 144-26 | 24.46 | 47.7 | 23.24 | 23.74 |
| 144-27 | 22.36 | 48.71 | 26.35 | 21.77 |
| 144-28 | 22.82 | 47.1 | 24.28 | 22.29 |
| 144-29 | 19.09 | 46.56 | 27.47 | 18.75 |
| 144-30 | 21.69 | 45.98 | 24.29 | 21.14 |
| 144-31 | 19.02 | 46.96 | 27.94 | 18.65 |
| 144-32 | 20.42 | 47.49 | 27.07 | 20.09 |
| 144-33 | 22.31 | 46.32 | 24.01 | 21.53 |
| 144-34 | 19.79 | 46.2 | 26.41 | 19.48 |
| 144-35 | 24.08 | 49.41 | 25.33 | 23.58 |
| 144-36 | 21.97 | 47.48 | 25.51 | 21.35 |
| 144-37 | 20.64 | 47.13 | 26.49 | 20.07 |
| 144-38 | 19.93 | 45.15 | 25.22 | 19.4 |
| 144-39 | 23.27 | 47.18 | 23.91 | 22.54 |
| 144-40 | 19.61 | 47.56 | 27.95 | 19.21 |
| 144-41 | 21.53 | 48.06 | 26.53 | 20.98 |
| 144-42 | 22.26 | 44.31 | 22.05 | 21.69 |
| 144-43 | 22.5 | 48.91 | 26.41 | 21.97 |
| 144-44 | 20.21 | 46.56 | 26.35 | 19.74 |

After 14 days the stakes were weighed, the results recorded, and returned to the humidity chamber. After a total of 21 days in the chamber, the stakes were weighed and the results recorded (AWPA Standard, Method E7-01, Sec. 6).

The treated stakes, as well as untreated control stakes, were environmentally tested also as described in Example 1D. After 6, 12, 17, 23, and 29 months, the stakes were removed from the ground and visually graded for decay according to AWPA protocol E7-01. After each assessment, the stakes were returned to their original position in the ground. As given in Table 18, the average decay score for ten treated stakes located in the Hialeah, Fla. test site was 8.9. The average score for ten untreated control stakes at this site was 0.

TABLE 18

Decay gradings of Fahlstrom stakes treated with
ammoniacal solution of copper/tungstate complex
(prepared in Example 3A), containing 1485 ppm of copper
and 5792 ppm of tungstate ion, tested in Hialeah, FL.

| Installed Mar. 15, 2004 Treatment | StakeID | Grading date/experimental time point/score | | | | |
|---|---|---|---|---|---|---|
| | | Sep. 21, 2004 6 mo | Feb. 15, 2005 12 mo | Aug. 17, 2005 17 mo | Feb. 2, 2006 23 mo | Aug. 1, 2006 29 mo |
| 1485 ppm Cu/5792 ppm WO$_4$ | 144_02 | 10 | 10 | 10 | 10 | 9.5 |
| | 144_05 | 10 | 10 | 10 | 9 | 9 |
| | 144_08 | 10 | 10 | 10 | 10 | 8 |
| | 144_10 | 10 | 10 | 10 | 10 | 9 |
| | 144_14 | 10 | 10 | 10 | 10 | 9 |
| | 144_22 | 10 | 10 | 10 | 10 | 9 |
| | 144_25 | 10 | 10 | 10 | 10 | 9 |
| | 144_33 | 10 | 10 | 10 | 10 | 8 |
| | 144_37 | 10 | 10 | 10 | 10 | 9 |
| | 144_39 | 10 | 10 | 10 | 10 | 9.5 |
| | Avg | 10 | 10 | 10 | 9.9 | 8.9 |
| | SD | 0 | 0 | 0 | 0.3 | 0.49 |
| Control Stakes (Untreated) | 143_11 | 10 | 9 | 0 | 0 | 0 |
| | 143_12 | 4 | 0 | 0 | 0 | 0 |
| | 143_13 | 8 | 10 | 0 | 0 | 0 |
| | 143_14 | 7 | 7 | 0 | 0 | 0 |
| | 143_15 | 8 | 4 | 0 | 0 | 0 |
| | 143_16 | 0 | 0 | 0 | 0 | 0 |
| | 143_17 | 8 | 9 | 0 | 0 | 0 |
| | 143_18 | 6 | 0 | 0 | 0 | 0 |
| | 143_19 | 6 | 4 | 0 | 0 | 0 |
| | 143_20 | 7 | 6 | 0 | 0 | 0 |
| | Avg | 6.4 | 4.9 | 0 | 0 | 0 |
| | SD | 2.62 | 3.73 | 0 | 0 | 0 |

The treated stakes much showed less decay than the untreated control stakes.

In a similar manner, Fahlstrom Stakes were prepared with the same treatment and environmentally tested at three additional sites. A summary of the results are given in Table 19 as averages of gradings at each site, including the Hialeah site.

TABLE 19

Averages of gradings of Fahlstrom stakes treated with
ammoniacal solution of 1485 ppm Cu/5792 ppm WO$_4$
(prepared in Example 3A) and tested at different sites.

| | | Treatment | | | |
|---|---|---|---|---|---|
| | | 1485 Cu/5792 WO$_4$ | | None - Control | |
| Location | Time (Months) | Avg Decay | Avg Insect damage | Avg Decay | Avg Insect damage |
| Hialeah, FL | 23 | 9.9 | xxx | 0 | xxx |
| LaPlace, LA | 24 | 7.85 | 8.7 | 2.85 | 3.7 |
| Starke, FL | 18 | 10 | 10 | 4.8 | 4.4 |
| Newark, DE | 24 | 9.45 | 9.9 | 6.75 | 8.13 | xxx means no insect attack observed at that site.

Example 4

Ammoniacal Solution of Copper/Molybdate Complex as Preservative

A) Preparation of Copper/Molybdate Complex in Ammoniacal Solution

A solution of 2.60 g of copper sulfate pentahydrate (0.0104 mol), 2.52 g of sodium molybdate dihydrate (0.0104 mol), 15 g of conc. ammonium hydroxide (57% ammonium hydroxide in water), and 778 g of water was prepared. To this solution was added enough water to prepare 1 Kg of wood treatment solution containing 662 ppm of copper and 1667 ppm of molybdate ion.

B) Penetration of Ammoniacal Solution of Copper/Molybdate Complex in Wood Blocks The ammoniacal solution of copper/molybdate complex prepared as described in Example 4A was imbibed into wood as described in Example 1B. Table 20 shows that the blocks gained weight, which indicated that the imbibing was successful.

TABLE 20

Solution retention in wood blocks treated with
ammoniacal solution of copper/molybdate complex.

| ID# | Dry wt (g) | Wet wt (g) | Gross retention (g) | |
|---|---|---|---|---|
| E2000111.00129A1 | 4.0361 | 8.7724 | 4.7363 | |
| E2000111.00129A2 | 3.9628 | 8.6573 | 4.6945 | |
| E2000111.00129A3 | 3.9823 | 7.6006 | 3.6183 | |
| E2000111.00129A4 | 3.9868 | 8.8000 | 4.8132 | |
| E2000111.00129A5 | 3.8200 | 9.0564 | 5.2364 | |
| E2000111.00129A6 | 3.9813 | 8.6649 | 4.6836 | |
| E2000111.00129A7 | 3.8717 | 8.5746 | 4.7029 | * |
| E2000111.00129A8 | 3.9407 | 8.5862 | 4.6455 | |
| E2000111.00129A9 | 3.7484 | 7.5529 | 3.8045 | |
| E2000111.00129A10 | 3.7840 | 7.6495 | 3.8655 | |
| E2000111.00129A11 | 3.7408 | 7.3497 | 3.6089 | |
| E2000111.00129A12 | 3.9122 | 8.8592 | 4.9470 | |
| E2000111.00129A13 | 3.7672 | 8.4705 | 4.7033 | * |
| E2000111.00129A14 | 4.0878 | 8.6734 | 4.5856 | |
| E2000111.00129A15 | 3.8482 | 8.8224 | 4.9742 | |
| E2000111.00128A16 | 3.7298 | 8.4051 | 4.6753 | |

TABLE 20-continued

Solution retention in wood blocks treated with ammoniacal solution of copper/molybdate complex.

| ID# | Dry wt (g) | Wet wt (g) | Gross retention (g) | |
|---|---|---|---|---|
| E2000111.00129A17 | 3.8652 | 8.5274 | 4.6622 | |
| E2000111.00129A18 | 4.0086 | 8.7178 | 4.7092 | * |
| E2000111.00129A19 | 3.7042 | 8.4616 | 4.7574 | |
| E2000111.00129A20 | 4.0289 | 8.8821 | 4.8532 | |
| E2000111.00129A21 | 4.0454 | 8.7642 | 4.7188 | * |
| E2000111.00129A22 | 3.9014 | 8.8184 | 4.9170 | |
| E2000111.00129A23 | 3.9778 | 8.8654 | 4.8876 | |
| E2000111.00129A24 | 3.7841 | 8.8195 | 5.0354 | |
| E2000111.00129A25 | 3.9195 | 8.8526 | 4.9331 | |
| E2000111.00129A26 | 3.8734 | 8.6006 | 4.7272 | * |
| E2000111.00129A27 | 3.9598 | 8.7771 | 4.8173 | |
| E2000111.00129A28 | 4.0155 | 8.6364 | 4.6209 | |
| E2000111.00129A29 | 3.8963 | 9.0759 | 5.1796 | |
| E2000111.00129A30 | 3.7046 | 7.7767 | 4.0721 | |
| E2000111.00129A31 | 3.9202 | 8.6315 | 4.7113 | * |
| E2000111.00129A32 | 3.8683 | 8.5167 | 4.6484 | |
| Used Cu/MoO$_4$ complex | 124.6733 | | 84.6129 | |

* marks blocks having a gross retention falling within +/−5% of the group average The blocks were then dried at room temperature for 2 weeks, and were again conditioned for 21 days in a humidity chamber set at 23° C.+/−0.5° C. and relative humidity of 50%+/−2%. From the 32 SYP blocks treated as above, six blocks having a gross retention falling within +/−5% of the group average were chosen. These blocks were chosen from those marked with an asterisk in Column 5 of Table 20 and are listed in Table 21.

TABLE 21

Weights of SYP wood blocks at different stages of treatment.

| ID number | initial wt (g) | wt after imbibing (g) | wt gain (g) |
|---|---|---|---|
| E2000111.00129A7 | 3.8717 | 8.5746 | 4.7029 |
| E2000111.00129A13 | 3.7672 | 8.4705 | 4.7033 |
| E2000111.00129A18 | 4.0086 | 8.7178 | 4.7092 |
| E2000111.00129A21 | 4.0454 | 8.7642 | 4.7188 |
| E2000111.00129A26 | 3.8734 | 8.6006 | 4.7272 |
| E2000111.00129A31 | 3.9202 | 8.6315 | 4.7113 |
| Total | 23.4865 | | 28.2727 |

The amount of copper contained in the six wood blocks was calculated based on the weight of treatment solution contained and the weight fraction of active ingredient in the treatment solution.

The total uptake of imbibing solution for the six blocks was 28.2727 g (see Table 21). The concentration of copper in the imbibing solution was 662 ppm. Therefore, the total amount of copper in the six blocks was (28.2727 g)(662 ppm)/1,000,000=0.01872 g copper. The total amount of molybdate ion in the six blocks was (28.2727 g)(1667 ppm)/1,000,000=0.04713 g of molybdate ion.

C) Retention of Ammoniacal Solution of Copper/Molybdate Complex in Wood

The six selected blocks imbibed with the ammoniacal solution of copper/molybdate complexes were tested for leaching as described in Example 1C, omitting the titration step. The remaining copper content of the blocks was analyzed by ashing. The blocks were allowed to dry at room temperature, and then all six blocks were heated together at 250° C. for 2 hours, then at 580° C. for 14 hours. The copper content of the ash was determined by XRF. The ash weighed 0.0610 g and contained 33.24% copper. The total amount of copper in the leached blocks was then (0.0610 g)(0.3324)=0.0203 g. By retention calculations, the initial amount of copper was 0.01872 g. This indicates that little or no copper was leached from the blocks. This result shows that there was excellent retention of copper in the wood when the copper is complexed as an ammoniacal solution of copper/molybdate Example 5

Ammoniacal Solution of Zinc/Molybate Complex as Preservative

A) Preparation of Zinc/Molybate Complex in Ammoniacal Solution

A solution of 1.912 g of zinc acetate, 15 g of conc. ammonium hydroxide (57% ammonium hydroxide in water), 2.52 g of sodium molybdate dihydrate, and 25 g of water was prepared. To this solution was added enough water to prepare 1 Kg of wood treatment solution containing 682 ppm of zinc and 1666 ppm of molybdate ion.

B) Penetration of Ammoniacal Solution of Zinc/molybdate Complex in Wood Blocks

The ammoniacal solution of zinc/molybdate complex prepared as described in Example 5A was imbibed into wood as described in Example 1B. Results in Table 22 show that the blocks gained weight, which indicated that the imbibing was successful.

TABLE 22

Solution retention in wood blocks treated with ammoniacal solution of zinc/molybdate complex.

| ID# | Dry wt (g) | Wet wt (g) | Gross retention (g) | |
|---|---|---|---|---|
| E2000111.00131A1 | 3.7793 | 8.9024 | 5.1231 | |
| E2000111.00131A2 | 4.0022 | 7.8522 | 3.8500 | |
| E2000111.00131A3 | 3.7985 | 8.9068 | 5.1083 | |
| E2000111.00131A4 | 4.0719 | 8.9711 | 4.8992 | |
| E2000111.00131A5 | 3.8262 | 9.0858 | 5.2596 | |
| E2000111.00131A6 | 3.7968 | 8.7155 | 4.9187 | |
| E2000111.00131A7 | 3.8646 | 8.9567 | 5.0921 | |
| E2000111.00131A8 | 3.8575 | 8.9501 | 5.0926 | |
| E2000111.00131A9 | 4.0863 | 8.9846 | 4.8983 | |
| E2000111.00131A10 | 3.9737 | 8.8389 | 4.8652 | |
| E2000111.00131A11 | 3.7030 | 8.7502 | 5.0472 | |
| E2000111.00131A12 | 3.8850 | 8.7008 | 4.8158 | * |
| E2000111.00131A13 | 3.8459 | 7.8645 | 4.0186 | |
| E2000111.00131A14 | 3.9943 | 8.7135 | 4.7192 | * |
| E2000111.00131A15 | 3.9918 | 8.9452 | 4.9534 | |
| E2000111.00131A16 | 3.7827 | 9.0908 | 5.3081 | |
| E2000111.00131A17 | 3.8108 | 8.7228 | 4.9120 | |
| E2000111.00131A18 | 3.8216 | 8.8194 | 4.9978 | |
| E2000111.00131A19 | 3.7526 | 8.8389 | 5.0863 | |
| E2000111.00131A20 | 3.8504 | 7.8691 | 4.0187 | |
| E2000111.00131A21 | 3.8476 | 7.9784 | 4.1308 | |
| E2000111.00131A22 | 4.0983 | 8.8454 | 4.7471 | |
| E2000111.00131A23 | 3.9413 | 7.5741 | 3.6328 | |
| E2000111.00131A24 | 3.9020 | 8.8174 | 4.9154 | * |
| E2000111.00131A25 | 3.9289 | 8.6511 | 4.7222 | * |
| E2000111.00131A26 | 4.0371 | 8.9542 | 4.9171 | |
| E2000111.00131A27 | 3.9639 | 8.9992 | 5.0353 | |
| E2000111.00131A28 | 3.9497 | 8.5945 | 4.6448 | * |

TABLE 22-continued

Solution retention in wood blocks treated with ammoniacal solution of zinc/molybdate complex.

| ID# | Dry wt (g) | Wet wt (g) | Gross retention (g) | |
|---|---|---|---|---|
| E2000111.00131A29 | 4.0782 | 9.2192 | 5.1410 | |
| E2000111.00131A30 | 3.7283 | 7.5528 | 3.8245 | |
| E2000111.00131A31 | 3.9296 | 8.6945 | 4.7649 | * |
| E2000111.00131A32 | 3.9565 | 8.7422 | 4.7857 | |
| | 124.8565 | 277.1023 | 152.2458 | |

* marks blocks having a gross retention falling within +/−5% of the group average The blocks were then dried at room temperature for 2 weeks, and were again conditioned for 21 days in a humidity chamber set at 23° C.+/−0.5° C. and relative humidity of 50%+/−2%. From the 32 SYP blocks treated as above, six blocks having a gross retention falling within +/−5% of the group average were chosen. These blocks were chosen from those marked with an asterisk in Column 5 of Table 22, and are listed in Table 23.

TABLE 23

Weights of SYP wood blocks at different stages of treatment.

| ID# | Dry wt (g) | Wet wt (g) | Gross retention (g) |
|---|---|---|---|
| E2000111.00131A12 | 3.8850 | 8.7008 | 4.8158 |
| E2000111.00131A14 | 3.9943 | 8.7135 | 4.7192 |
| E2000111.00131A24 | 3.9020 | 8.8174 | 4.9154 |
| E2000111.00131A25 | 3.9289 | 8.6511 | 4.7222 |
| E2000111.00131A28 | 3.9497 | 8.5945 | 4.6448 |
| E2000111.00131A31 | 3.9296 | 8.6945 | 4.7649 |
| Total | 23.5895 | 52.1718 | 28.5823 |

The amounts of active ingredients contained in the six wood blocks was calculated based on the weight of treatment solution contained and the weight fraction of active ingredients in the treatment solution. The total uptake of imbibing solution for these six blocks was 28.5823 g (see Table 23). The concentration of zinc in the imbibing solution was 681 ppm. Therefore, the total amount of zinc and molybdate in the six blocks was (28.5823 g)(681 ppm)/1,000,000=0.0195 g zinc and (28.5823)(1666 ppm)/1,000,000=0.0476 g of molybdate.

C) Retention of Ammoniacal Solution of Zinc/Molybdate Complex in Wood

The six selected blocks imbibed with the ammoniacal solution of zinc/molybdate complexes were tested for leaching as described in Example 1C, omitting the titration step. The remaining zinc content of the blocks was analyzed by ashing. The blocks were allowed to dry at room temperature, and then all six blocks were heated together at 250° C. for 2 hours, then at 580° C. for 14 hours. The ash weighed 0.0576 g and contained 37.95% zinc by XRF analysis. The total amount of zinc remaining in the leached blocks was 0.0218 g. By retention calculations, the initial amount of zinc was 0.0195 g. This indicates that little or no zinc was leached from the blocks. This result shows that there was excellent retention of zinc in the wood when the zinc is complexed as an ammoniacal solution of zinc/molybdate.

Example 6

Ammoniacal Solution of Zinc/Tungstate Complex as Preservative

A) Preparation of Zinc/Tungstate Complex in Ammoniacal Solution

A solution of 1.00 g of zinc acetate, 15 g of conc. ammonium hydroxide (57% ammonium hydroxide in water), 1.798 g of sodium tungstate dihydrate, and 25 g of water was prepared. To this solution was added enough water to prepare 1 Kg of wood treatment solution containing 356 ppm of zinc and 1351 ppm of tungstate ion.

B) Penetration of Ammoniacal Solution of Zinc/Tungstate Complex in Wood Blocks

The ammoniacal solution of zinc/tungstate complex prepared as above was imbibed into wood as described in Example 1B. Results in Table 24 show that the blocks gained weight, which indicated that the imbibing was successful.

TABLE 24

Gross Retention in SYP wood blocks treated with ammoniacal solution of zinc/tungstate complex.

| ID# | Dry wt (g) | Wet wt (g) | Gross retention (g) | |
|---|---|---|---|---|
| E2000111.00130A1 | 4.1072 | 8.8506 | 4.7434 | |
| E2000111.00130A2 | 4.0148 | 8.8067 | 4.7919 | |
| E2000111.00130A3 | 3.8692 | 8.6253 | 4.7561 | |
| E2000111.00130A4 | 3.7246 | 8.7395 | 5.0149 | |
| E2000111.00130A5 | 4.0181 | 8.7262 | 4.7081 | |
| E2000111.00130A6 | 3.8597 | 8.6950 | 4.8353 | |
| E2000111.00130A7 | 4.0038 | 8.7805 | 4.7767 | |
| E2000111.00130A8 | 4.0199 | 8.6019 | 4.5820 | |
| E2000111.00130A9 | 3.9093 | 8.5763 | 4.6670 | * |
| E2000111.00130A10 | 3.8570 | 9.0494 | 5.1924 | |
| E2000111.00130A11 | 3.9730 | 8.9246 | 4.9516 | |
| E2000111.00130A12 | 3.8687 | 8.9818 | 5.1131 | |
| E2000111.00130A13 | 3.9680 | 8.6646 | 4.6966 | * |
| E2000111.00130A14 | 3.8878 | 8.6979 | 4.8101 | |
| E2000111.00130A15 | 3.7669 | 8.6859 | 4.9190 | |
| E2000111.00130A16 | 3.9659 | 8.6800 | 4.7141 | * |
| E2000111.00130A17 | 3.8337 | 8.8793 | 5.0456 | |
| E2000111.00130A18 | 4.0911 | 8.9867 | 4.8956 | |
| E2000111.00130A19 | 3.9610 | 8.8211 | 4.8601 | |
| E2000111.00130A20 | 3.9615 | 8.5425 | 4.5810 | |
| E2000111.00130A21 | 3.8899 | 8.6380 | 4.7481 | * |
| E2000111.00130A22 | 3.9374 | 7.5336 | 3.5962 | |
| E2000111.00130A23 | 4.0768 | 8.7287 | 4.6519 | |
| E2000111.00130A24 | 3.9365 | 8.6971 | 4.7606 | * |
| E2000111.00130A25 | 4.0658 | 9.0371 | 4.9713 | |
| E2000111.00130A26 | 3.8236 | 8.8318 | 5.0082 | |
| E2000111.00130A27 | 3.8218 | 8.7098 | 4.8880 | |
| E2000111.00130A28 | 3.7648 | 8.6917 | 4.9269 | |
| E2000111.00130A29 | 4.0132 | 8.2722 | 4.2590 | |
| E2000111.00130A30 | 4.0158 | 8.7397 | 4.7239 | |
| E2000111.00130A31 | 3.8784 | 8.6842 | 4.8058 | * |
| E2000111.00130A32 | 3.7953 | 9.0382 | 5.2429 | |
| | 125.6805 | | 153.2374 | |

* marks blocks having a gross retention falling within +/−5% of the group average The blocks were then dried at room temperature for 2 weeks, and were again conditioned for 21 days in a humidity chamber set at 23° C.+/−0.5° C. and relative humidity of 50%+/−2%. From the 32 SYP blocks treated as above, six blocks having a gross retention falling within +/−5% of the group average were chosen. These blocks were chosen from those marked with an asterisk in Column 5 of Table 24 and are listed in Table 25.

TABLE 25

Weights of SYP wood blocks at different stages of treatment.

| ID# | Dry wt (g) | Wet wt (g) | Gross retention (g) |
|---|---|---|---|
| E2000111.00130A9 | 3.9093 | 8.5763 | 4.667 |
| E2000111.00130A13 | 3.9680 | 8.6646 | 4.6966 |
| E2000111.00130A16 | 3.9659 | 8.6800 | 4.7141 |
| E2000111.00130A21 | 3.8899 | 8.6380 | 4.7481 |
| E2000111.00130A24 | 3.9365 | 8.6971 | 4.7606 |
| E2000111.00130A31 | 3.8784 | 8.6842 | 4.8058 |
| | 23.5480 | | 28.3922 |

The amounts of active ingredients contained in the six wood blocks was calculated based on the weight of treatment solution contained and the weight fraction of active ingredient in the treatment solution. The total uptake of imbibing solution for these six blocks was 28.3922 g (see Table 25). The concentration of zinc in the imbibing solution was 356 ppm. Therefore, the total amount of zinc and tungstate in the six blocks was (28.3922 g)(356 ppm)/1,000,000=0.0101 g zinc and (28.3922)(1351 ppm)/1,000,000=0.03838 g of tungstate.

C) Retention of Ammoniacal Solution of Zinc/Tungstate Complex in Wood Blocks

The six selected blocks imbibed with the ammoniacal solution of zinc tungstate complexes were tested for leaching as described in Example 1C, omitting the titration.

The blocks were ashed as described in Example 5C and zinc content determined by XRF. The ash weighed 0.0620 g and contained 19.94% zinc. The total amount of zinc remaining in the leached blocks was 0.0101 g. By retention calculations, the initial amount of zinc was 0.0124 g. This indicates that little zinc was leached from the blocks. This result shows that there was excellent retention of zinc in the wood when the zinc is complexed as an ammoniacal solution of zinc/tungstate.

Example 7

Ammoniacal Solution of Hydrolyzed Octene/Maleic Anhydride Copolymer and Copper/Tungstate Complex as Preservative A) Preparation of Hydrolyzed Octene/Maleic Anhydride Copolymer and Copper/Tungstate Complex in Ammoniacal Solution A solution of 116.7 g of copper sulfate pentahydrate, 13.2 g of sodium tungstate dihydrate, 250 g of conc. ammonium hydroxide (57% ammonium hydroxide), and 345 g of water was prepared. To this was added 394.7 g of a 27.1% solution of hydrolyzed octane/maleic anhydride copolymer monosodium salt (prepared as described in General Methods) to prepare a concentrated wood preservation solution. The solution was then diluted with 1.4% aqueous ammonium hydroxide solution to prepare 20 Kg of a wood preservation solution that contained 1485 ppm of copper and 496 ppm of tungstate ion.

D) Preparation and Environmental Testing of Decay Stakes Treated with Ammoniacal Solution of Hydrolyzed Octene/Maleic Anhydride Copolymer and Copper/Tungstate Complex Ten pre-decay stakes were prepared and treated with the solution prepared in Example 7A as described in Example 1D. The uptake of treatment solution was evident from the results displayed in Table 26.

TABLE 26

Retention of Treatment Solution in SYP Pre-Decay Stakes.

| Stake ID | Dry wt (g) | Wet wt (g) | Gross retention (g) |
|---|---|---|---|
| W0897 | 216.18 | 464.98 | 248.8 |
| W0899 | 223.63 | 459.54 | 235.91 |
| W0901 | 213.18 | 460.67 | 247.49 |
| W0903 | 214.87 | 455.45 | 240.58 |
| W0905 | 215.15 | 458.96 | 243.81 |
| W0907 | 223.9 | 466.73 | 242.83 |
| W0909 | 210.56 | 462.36 | 251.8 |
| W0911 | 226.63 | 477.27 | 250.64 |
| W0913 | 215.52 | 463.2 | 247.68 |
| W0915 | 227.8 | 457.82 | 230.02 |

The ten labeled stakes were cut into decay stakes of 45.7 cm (18") lengths, cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Pre-decay stakes were similarly prepared and treated with 1:2 and 1:4 dilutions of the treatment solution prepared in Example 7A. Decay stakes were cut as described above and stakes prepared with undiluted and diluted treatment solutions were placed in the ground in Newark, Del. and Starke, Fla. per AWPA E7-01, as described in Example 1E. After 12 months, the stakes in Newark, Del. were removed from the ground and visually graded for decay and termite attack according to AWPA protocol E7-01. The results are given in Table 27. Stakes at Starke, Fla. are removed and assessed at a later date.

TABLE 27

Decay and insect damage data for stakes treated with different dilutions of ammoniacal solution of hydrolyzed OMA and copper/tungstate complex tested in Newark, DE.

| | | 12 mo scores | |
|---|---|---|---|
| Treatment | Stake ID | Decay | Insect damage |
| 1485 ppm Copper/496 ppm WO₄/hydrolyzed OMA | W0897 | 10 | 9.5 |
| | W0899 | 10 | 10 |
| | W0901 | 10 | 10 |
| | W0903 | 10 | 10 |
| | W0905 | 10 | 10 |
| | W0907 | 10 | 10 |
| | W0909 | 10 | 10 |
| | W0911 | 10 | 10 |
| | W0913 | 10 | 10 |
| | W0915 | 10 | 10 |
| | Avg | 10 | 9.95 |
| | SD | 0 | 0.15 |
| 742 ppm Copper/248 ppm WO₄/hydrolyzed OMA | W0967 | 10 | 9.5 |
| | W0969 | 10 | 10 |
| | W0971 | 10 | 10 |
| | W0973 | 10 | 10 |
| | W0975 | 10 | 10 |
| | W0977 | 10 | 10 |
| | W0979 | 10 | 10 |
| | W0981 | 10 | 10 |
| | W0983 | 10 | 10 |

TABLE 27-continued

Decay and insect damage data for stakes treated with different dilutions of ammoniacal solution of hydrolyzed OMA and copper/tungstate complex tested in Newark, DE.

| | | 12 mo scores | |
|---|---|---|---|
| Treatment | Stake ID | Decay | Insect damage |
| | W0985 | 10 | 10 |
| | Avg | 10 | 9.95 |
| | SD | 0 | 0.15 |
| 371 ppm Copper/124 ppm WO$_4$/hydrolyzed OMA | W0987 | 10 | 10 |
| | W0989 | 10 | 10 |
| | W0991 | 10 | 10 |
| | W0993 | 10 | 10 |
| | W0995 | 10 | 10 |
| | W0997 | 10 | 10 |
| | W0999 | 9.5 | 10 |
| | W1001 | 10 | 10 |
| | W1003 | 10 | 10 |
| | W1005 | 10 | 10 |
| | Avg | 9.95 | 10 |
| | SD | 0.15 | 0 |
| Untreated Controls | W1439 | 10 | 10 |
| | W1441 | 8 | 10 |
| | W1443 | 8 | 8 |
| | W1445 | 8 | 10 |
| | W1447 | 9.5 | 9.5 |
| | W1449 | 9.5 | 10 |
| | W1451 | 10 | 10 |
| | W1453 | 8 | 10 |
| | W1455 | 8 | 10 |
| | W1457 | 9 | 10 |
| | Avg | 8.8 | 9.75 |
| | SD | 0.84 | 0.60 |

Since there was little decay and insect damage at the Newark site in 12 months, the differences between the treated and control stakes are small. It is expected that over longer periods of time, the differences will be greater at this site.

Fahlstrom Stakes were prepared and tested as described in Example 1D using the solution prepared in Example 7A. The stakes were graded for decay after 6 and 12 months and the results are given in Table 28. After 12 months, the average score for the ten treated stakes was 9.55, while the average score for untreated control stakes was 3.9. Thus the Fahlstrom Stakes treated with the test solution showed much less fungal decay than the untreated control stakes.

TABLE 28

Decay grading of Fahlstrom Stakes treated with ammoniacal solution of hydrolyzed octene/maleic anhydride copolymer and copper/tungstate complex, containing 1485 ppm of copper and 496 ppm of tungstate ion, tested at Hialeah, FL.

| | | Grading date/experimental time point/score | |
|---|---|---|---|
| Installed Aug. 19, 2005 Treatment | Stake ID | Feb. 2, 2006 6 mo | Aug. 1, 2006 12 mo |
| 1458 ppm Cu/496 ppm WO$_4$/ hydrolyzed OMA | 218-01 | 9 | 10 |
| | 218-13 | 10 | 7 |
| | 218-14 | 10 | 10 |
| | 218-15 | 10 | 10 |
| | 218-21 | 10 | 9.5 |
| | 218-25 | 10 | 9.5 |
| | 218-26 | 10 | 10 |
| | 218-33 | 10 | 9.5 |
| | 218-43 | 10 | 10 |
| | 218-44 | 10 | 10 |
| | Avg | 9.9 | 9.55 |
| | SD | 0.3 | 0.88 |

TABLE 28-continued

Decay grading of Fahlstrom Stakes treated with ammoniacal solution of hydrolyzed octene/maleic anhydride copolymer and copper/tungstate complex, containing 1485 ppm of copper and 496 ppm of tungstate ion, tested at Hialeah, FL.

| | | Grading date/experimental time point/score | |
|---|---|---|---|
| Installed Aug. 19, 2005 Treatment | Stake ID | Feb. 2, 2006 6 mo | Aug. 1, 2006 12 mo |
| Untreated Control Stakes | 230-01 | 6 | 4 |
| | 230-02 | 8 | 4 |
| | 230-03 | 6 | 0 |
| | 230-04 | 9 | 7 |
| | 230-05 | 6 | 4 |
| | 230-06 | 7 | 4 |
| | 230-07 | 7 | 4 |
| | 230-08 | 7 | 4 |
| | 230-09 | 9 | 8 |
| | 230-10 | 6 | 0 |
| | Avg | 7.1 | 3.9 |
| | SD | 1.14 | 2.39 |

In a similar manner, Fahlstrom Stakes were prepared with the same treatment and environmentally tested at three additional sites. A summary of the results are given in Table 29 as averages of gradings at each site, including the Hialeah site.

TABLE 29

Averages of gradings of Fahlstrom stakes treated with 1485 ppm Cu/496 ppm WO$_4$/OMA (prepared in Example 7A) and tested at different sites.

| | | Treatment | | | |
|---|---|---|---|---|---|
| | | 1485 Cu/496 WO$_4$/hudrolyzed OMA | | None - control | |
| Location | Time (Months) | Avg Decay | Avg Insect damage | Avg Decay | Avg Insect damage |
| Hialeah, FL | 12 | 9.55 | xxx | 3.9 | xxx |
| LaPlace, LA | 6 | 9.65 | 10 | 8.9 | 9.95 |
| Starke, FL | 12 | 9.8 | 9.8 | 6.05 | 5.7 |
| Newark, DE | 12 | 9.85 | 9.9 | 7.94 | 9.39 | xxx means no insect attack observed at that site.

With substantial decay to controls at Hialeah, and substantial decay and insect damage at Starke, good protection by the treatment solution was observed at these sites. Since there was little decay and insect damage at the Newark and LaPlace sites in 12 and 6 months, respectively, the differences between the treated and control stakes are small. It is expected that over longer periods of time, the differences will be greater at these sites.

Example 8

Ammoniacal Solution of CE-Sorb6 Amidoxime and Copper/Tungstate Complex as Preservative A) Preparation of CE-Sorb6 Amidoxime and Copper/Tungstate Complex in Ammoniacal Solution A solution of 116.7 g of copper sulfate pentahydrate, 13.3 g of sodium tungstate dihydrate, 150 g of conc. ammonium hydroxide (57% ammonium hydroxide), and 250 g of water was prepared. To this was added 91.8 g of a 57% solution of the amidoxime of CE-Sorb6 having a DS=5.6 (prepared as described in General Methods). The mixture was stirred for 30 minutes at room temperature to prepare a concentrated wood preservation solution. The concentrated solution was then diluted to a final weight of 20 Kg with 1.4% aqueous ammonium hydroxide solution to prepare a wood preservation solution having 1485 ppm copper and 500 ppm tungstate ion.

D) Preparation and Environmental Testing of Decay Stakes Treated with Ammoniacal Solution of Amidoxime of CE-Sorb6 and Copper/Tungstate Complex Ten pre-decay stakes were prepared and treated with the solution prepared in Example 8A as described in Example 1D. The uptake of treatment solution was evident from the results (positive weight gain) displayed in Table 30.

TABLE 30

Retention of Treatment Solution in SYP Pre-Decay Stakes.

| Stake ID | Dry wt (g) | Wet wt (g) | Gross retention (g) |
|---|---|---|---|
| W1819 | 216.42 | 452.26 | 235.84 |
| W1821 | 195.81 | 440.32 | 244.51 |
| W1823 | 201.43 | 447.9 | 246.47 |
| W1825 | 200.8 | 453.05 | 252.25 |
| W1827 | 209.57 | 459.59 | 250.02 |
| W1829 | 189.31 | 439.95. | 250.64 |
| W1831 | 199.19 | 447.17 | 247.98 |
| W1833 | 208.95 | 454.77 | 245.82 |
| W1835 | 197.23 | 452.67 | 255.44 |
| W1837 | 215.91 | 466.11 | 250.2 |

The ten labeled stakes were cut into decay stakes of 45.7 cm (18") lengths, cutting from each end and leaving a 5.1 cm (2") witness section from the center of the stake. All witness sections were tested for copper penetration using the Chromazurol S test described in the General Methods. All witness sections tested turned dark blue indicating complete penetration of the wood by the wood preservative treatment solution.

Decay stakes were similarly prepared and treated with 1:2 and 1:4 dilutions of the wood preservative treatment solution prepared in Example 8A.

The stakes were placed in the ground in Newark, Del. as per AWPA E7-01, described in Example 1E. After 12 months, the stakes were removed from the ground and visually graded for rot and termite attack according to AWPA protocol E7-01. The results are given in Table 31.

TABLE 31

Averages of gradings of decay stakes treated with different dilutions of ammoniacal solution of CE-Sorb6 amidoxime and copper/tungstate complex

| Location | Conc. (ppm) | Time (Months) | Avg Decay | Avg Insect damage |
|---|---|---|---|---|
| Newark, DE | Cu(1485)/WO4(500)/CE-Sorb6 amidoxime | 12 | 10 | 10 |
| | Cu(742)/WO4(250)/CE-Sorb6 amidoxime | 12 | 10 | 10 |
| | Cu(371)/WO4(125)/CE-Sorb6 amidoxime | 12 | 9.9 | 10 |
| | Control | 12 | 8.8 | 9.8 |

Since there was little decay and insect damage at the Newark site in 12 months, the differences between the treated and control stakes are small. It is expected that over longer periods of time, treated stakes will show less decay and insect damage with respect to controls at this site.

Fahlstrom Stakes were prepared and tested as described in Example 1D using the solution prepared in Example 8A. The stakes in Hialeah, Fla. were graded for decay after 6 and 12 months and the results are given in Table 32. After 12 months, the average score for the ten treated stakes was 9.8, while the average score for the control stakes was 3.9. Thus the Fahlstrom stakes treated with the test solution showed much less fungal decay damage than untreated control stakes.

TABLE 32

Decay grading of Fahlstrom stakes treated with ammoniacal solution of CE-Sorb6 amidoxime and copper/tungstate complex.

| | | Grading date/experimental time point | |
|---|---|---|---|
| | | Feb. 2, 2006 | Aug. 1, 2006 |
| Installed Aug. 19, 2005 | | 6 mo | 12 mo |
| Treatment | Stake ID | Decay | Decay |
| 1485 ppm Cu/500 ppm WO4/ | 250-12 | 10 | 10 |
| CE-Sorb6 Amidoxime | 250-13 | 10 | 9.5 |
| | 250-14 | 10 | 10 |
| | 250-15 | 10 | 9.5 |
| | 250-16 | 10 | 10 |
| | 250-17 | 10 | 10 |
| | 250-18 | 10 | 10 |
| | 250-19 | 10 | 9 |
| | 250-20 | 10 | 10 |
| | 250-21 | 10 | 10 |
| | Avg | 10 | 9.8 |
| | SD | 0 | 0.33 |
| Untreated Control Stakes | 230-01 | 6 | 4 |
| | 230-02 | 8 | 4 |
| | 230-03 | 6 | 0 |
| | 230-04 | 9 | 7 |
| | 230-05 | 6 | 4 |
| | 230-06 | 7 | 4 |
| | 230-07 | 7 | 4 |
| | 230-08 | 7 | 4 |
| | 230-09 | 9 | 8 |
| | 230-10 | 6 | 0 |
| | Avg | 7.1 | 3.9 |
| | SD | 1.14 | 2.39 |

In a similar manner, Fahlstrom Stakes were prepared with the same treatment solution, as well as with 1:2 and 1:4 dilutions of this solution, and environmentally tested at three additional sites. Stakes treated with the diluted solution were also tested at Hialeah, Fla. A summary of the results are given in Table 33 as averages of gradings at each site (the 6 month Hialeah data for the undiluted solution is the same as in Table 32).

TABLE 33

Averages of gradings of Fahlstrom stakes treated with different dilutions of ammoniacal solution of CE-Sorb6 amidoxime and copper/tungstate complex at multiple locations

| Location | Conc. (ppm) | Time (Months) | Avg Decay | Avg Insect damage |
|---|---|---|---|---|
| Starke, FL | Cu(1485)/WO4(500)/CE Sorb6 amidoxime | 6 | 9.9 | 10 |
| | Cu(742)/WO4(250)/CE-Sorb6 amidoxime | 6 | 9.7 | 10 |
| | Cu(371)/WO4(125)/CE-Sorb6 amidoxime | 6 | 8.45 | 9.4 |
| | Control | 6 | 9.2 | 9.15 |
| Newark, | Cu(1485)/WO4(500)/CE- | 6 | 10 | 10 |

TABLE 33-continued

Averages of gradings of Fahlstrom stakes treated with
different dilutions of ammoniacal solution of CE-Sorb6
amidoxime and copper/tungstate complex at multiple
locations

| Location | Conc. (ppm) | Time (Months) | Avg Decay | Avg Insect damage |
|---|---|---|---|---|
| DE | Sorb6 amidoxime | | | |
| | Cu(742)/WO$_4$(250)/CE-Sorb6 amidoxime | 6 | 9.9 | 10 |
| | Cu(371)/WO$_4$(125)/CE-Sorb6 amidoxime | 6 | 9.9 | 10 |
| | Control | 6 | 8.2 | 9.9 |
| Hialeah, FL | Cu(1485)/WO$_4$(500)/CE-Sorb6 amidoxime | 6 | 10 | xxxx |
| | Cu(742)/WO$_4$(250)/CE-Sorb6 amidoxime | 6 | 10 | xxxx |
| | Cu(371)/WO$_4$(125)/CE-Sorb6 amidoxime | 6 | 9.9 | xxxx |
| | Control | 6 | 7.1 | xxxx |
| LaPlace, LA | Cu(1485)/WO$_4$(500)/CE-Sorb6 amidoxime | 6 | 9.9 | 10 |
| | Cu(742)/WO$_4$(250)/CE-Sorb6 amidoxime | 6 | 9.9 | 9.8 |
| | Cu(371)/WO$_4$(125)/CE-Sorb6 amidoxime | 6 | 9.2 | 10 |
| | Control | 6 | 8.9 | 9.9 | xxx means no insect attack observed at that site

Since there was little decay and insect damage in 6 months at the sites other than decay at Hialeah, the differences between the treated and control stakes are small at those sites. It is expected that over longer periods of time, treated stakes will show less decay and insect damage with respect to controls at those sites.

What is claimed is:

1. An aqueous composition comprising in admixture (a) a complex comprising (i) molybdate ions, tungstate ions or a mixture thereof, and (ii) copper ions, zinc ions or a mixture thereof; and (b) ammonia and/or ethanolamine; wherein component (b) is present in an amount sufficient to solubilize the complex; and wherein a molybdate ion, when present in component (a), is present in the absence or substantial absence of a quaternary ammonium salt; and wherein the composition further comprises at least one hydrolyzed olefin/maleic anhydride copolymer.

2. The composition of claim 1 wherein the complex comprises tungstate ions, or a mixture of molybdate ions and tungstate ions.

3. The composition of claim 1 wherein the copolymer is hydrolyzed octene/maleic anhydride copolymer, hydrolyzed styrene/maleic anhydride copolymer, or mixtures thereof.

4. The composition of claim 1 further comprising a copper chelating compound.

5. The composition of claim 1 further comprising a copper chelating compound comprising at least two functional groups selected from the group consisting of amidoxime, hydroxamic acid, thiohydroxamic acid, N-hydroxyurea, N-hydroxycarbamate, and N-nitroso-alkyl-hydroxylamine.

6. The composition of claim 4 wherein the chelating compound comprises at least two hydroxamic groups and the chelating compound is derived from styrene/maleic anhydride copolymer or octene/maleic anhydride copolymer.

7. The composition of claim 4 wherein the chelating compound comprises at least two functional groups selected from amidoxime and hydroxamic acid, and the amidoxime or hydroxamic acid is derived from a cyanoethylated compound.

8. The composition of claim 7 wherein the cyanoethylated compound is derived from the cyanoethylation of a primary amine, a secondary amine, blood albumin, casein, soybean protein, wool, or corn zein; or from materials derived from blood albumin, casein, gelatin, gluten, soybean protein, wool, or corn zein.

9. The composition of claim 7 wherein the cyanoethylated compound is derived from the cyanoethylation of synthetic polymers selected from the group consisting of acetone-formaldehyde condensate, acetone-isobutyraldehyde condensate, methyl ethyl ketone-formaldehyde condensate, poly(allyl alcohol), poly(crotyl alcohol), poly(3-chloroallyl alcohol), ethylene carbon monoxide copolymers, polyketone from propylene, ethylene and carbon monoxide, poly(methallyl alcohol), poly(methyl vinyl ketone), and poly(vinyl alcohol).

10. The composition of claim 7 wherein the cyanoethylated compound is obtained from the cyanoethylation of materials selected from the group of: alcohols, carbohydrates, dextran, dextrin, gums, starches, modified natural polymers; and compounds derived from natural polymers.

11. The composition of claim 7 wherein the cyanoethylated compound is obtained from the cyanoethylation of sucrose or sorbitol.

12. The composition of claim 1 further comprising a component (c) selected from one or both of an additional antifungal component and an additional a termiticidal component.

13. The composition of claim 12 wherein the component (c) is ibuprofen, a tropolone or mixtures thereof.

14. A process for preserving cellulosic material, or an article that comprises cellulosic material, comprising contacting the cellulosic material or the article with the composition of claim 1.

15. The process of claim 14 wherein the cellulosic material is selected from the group consisting of wood, lumber, plywood, oriented strand board, cellulose, hemicellulose, lignin, cotton, and paper.

16. The process of claim 14 which comprises dipping, brushing, spraying, draw-coating, rolling or pressure-treating the cellulosic material or article with the composition.

17. Cellulosic material, or an article comprising cellulosic material, wherein the composition of claim 1 is adsorbed on and/or absorbed in the cellullosic material.

18. The material or article of claim 17 wherein the cellulosic material is selected from the group consisting of wood, lumber, plywood, oriented strand board, cellulose, cotton, lignin, and hemicellulose.

19. A structure or consumable device comprising the cellulosic material or article of claim 17.

20. A process for preserving harvested cellulosic material, or an article that comprises harvested cellulosic material, comprising contacting the harvested cellulosic material or the article with an aqueous composition comprising in admixture (a) a complex comprising (i) molybdate ions, tungstate ions or a mixture thereof, and (ii) copper ions, zinc ions or a mixture thereof; and (b) ammonia and/or ethanolamine; wherein component (b) is present in an amount sufficient to solubilize the complex; and wherein a molybdate ion, when present in component (a), is present in the absence or substantial absence of a quaternary ammonium salt.

21. The process of claim 20 wherein the cellulosic material is selected from the group consisting of wood, lumber, plywood, oriented strand board, cellulose, hemicellulose, lignin, cotton, and paper.

22. The process of claim 20 which comprises dipping, brushing, spraying, draw-coating, rolling or pressure-treating the cellulosic material or article with the composition.

23. The process of claim 20 wherein the cellulosic material is wood or lumber.

24. The process of claim 23 further comprising subjecting the wood or lumber to vacuum before and/or after contacting the wood or lumber with the composition.

25. The process of claim 20 further comprising a step of incorporating the cellulosic material or the article into a structure or into a consumable device.

26. An article comprising cellulosic material, wherein there is adsorbed on and/or absorbed in the cellulosic material of the article an aqueous composition comprising in admixture (a) a complex comprising (i) molybdate ions, tungstate ions or a mixture thereof, and (ii) copper ions, zinc ions or a mixture thereof; and (b) ammonia and/or ethanolamine; wherein component (b) is present in an amount sufficient to solubilize the complex; and wherein a molybdate ion, when present in component (a), is present in the absence or substantial absence of a quarternary ammonium salt.

27. The article of claim 26 wherein the cellulosic material is selected from the group consisting of wood, lumber, plywood, oriented strand board, cellulose, cotton, lignin, and hemicellulose.

28. The article of claim 26 wherein the cellulosic material is selected from the group consisting of wood, lumber, plywood, oriented strand board, paper, cellulose, cotton, lignin, and hemicellulose; and the composition comprises a hydrolyzed olefin/maleic anhydride copolymer.

29. The article of claim 26 wherein the composition comprises a copper chelating compound.

30. The article of claim 29 wherein the copper chelating compound comprises at least two functional groups selected from the group consisting of amidoxime, hydroxamic acid, thiohydroxamic acid, N-hydroxyurea, N-hydroxycarbamate, and N-nitroso-alkyl-hydroxylamine.

31. The article of claim 29 wherein the copper chelating compound comprises at least two hydroxamic groups and is derived from styrene/maleic anhydride copolymer or octene/maleic anhydride copolymer.

32. The article of claim 29 wherein the copper chelating compound comprises at least two functional groups selected from amidoxime and hydroxamic acid, and the amidoxime or hydroxamic acid is derived from a cyanoethylated compound.

33. The article of claim 32 wherein the cyanoethylated compound is obtained from the cyanoethylation of sucrose or sorbitol.

34. The article of claim 26 wherein the composition further comprises a component (c) selected from one or both of an additional antifungal component and an additional termiticidal component.

35. A structure or consumable device comprising the article of claim 26.

36. An aqueous composition comprising in admixture (a) a complex comprising (i) tungstate ions, or a mixture molybdate ions and tungatate ions; (ii) copper ions, zinc ions or a mixture thereof; and (b) ammonia and/or ethanolamine; wherein component (b) is present in an amount sufficient to solubilize the complex; and wherein a molybdate ion, when present in component (a), is present in the absence or substantial absence of a quaternary ammonium salt.

37. The composition of claim 36 wherein component (a)(i) comprises tungstate ions.

38. The composition of claim 36 wherein component (a)(i) comprises a mixture of molybdate ions and tungatate ions.

39. The composition of claim 36 further comprising at least one hydrolyzed olefin/maleic anhydride copolymer.

40. The composition of claim 36 further comprising a copper chelating compound.

41. The composition of claim 36 further comprising a component (c) selected from one or both of an additional antifungal component and an additional a termiticidal component.

42. A process for preserving cellulosic material, or an article that comprises cellulosic material, comprising contacting the cellulosic material or the article with the composition of claim 36.

43. The process of claim 42 wherein the cellulosic material is selected from the group consisting of wood, lumber, plywood, oriented strand board, cellulose, hemicellulose, lignin, cotton, and paper.

44. The process of claim 42 which comprises dipping, brushing, spraying, draw-coating, rolling or pressure-treating the cellulosic material or article with the composition.

45. Cellulosic material, or an article comprising cellulosic material, wherein the composition of claim 36 is adsorbed on and/or absorbed in the cellulosic material.

46. The material or article of claim 45 wherein the cellulosic material is selected from the group consisting of wood, lumber, plywood, oriented strand board, cellulose, cotton, lignin, and hemicellulose.

47. A structure or consumable device comprising the cellulosic material or article of claim 45.

48. An aqueous composition comprising in admixture (a) a complex comprising (i) molybdate ions, tungstate ions or a mixture thereof, and (ii) zinc ions, or a mixture of copper ions and zinc ions; and (b) ammonia and/or ethanolamine; wherein component (b) is present in an amount sufficient to solubilize the complex; and wherein a molybdate ion, when present in component (a), is present in the absence or substantial absence of a quaternary animonium salt.

49. The composition of claim 48 wherein component (a)(ii) comprises zinc ions.

50. The composition of claim 48 wherein component (a)(ii) comprises a mixture of copper ions and zinc ions.

51. The composition of claim 48 further comprising at least one hydrolyzed olefin/maleic anhydride copolymer.

52. The composition of claim 50 further comprising a copper chelating compound.

53. The composition of claim 48 further comprising a component (c) selected from one or both of an additional antifungal component and an additional a termiticidal component.

54. A process for presenting cellulosic material, or an article that comprises cellulosic material, comprising contacting the cellulosic material or the article with the composition of claim 48.

55. The process of claim 54 wherein the cellulosic material is selected from the group consisting of wood, lumber, plywood, oriented strand board, cellulose, hemicellulose, lignin, cotton, and paper.

56. The process of claim 54 which comprises dipping, brushing, spraying, draw-coating, rolling or pressure-treating the cellulosic material or article with the composition.

57. Cellulosic material, or an article comprising cellulosic material, wherein the composition of claim 48 is adsorbed on and/or absorbed in the cellulosic material.

58. The material or article of claim 57 wherein the cellulosic material is selected from the group consisting of wood, lumber, plywood, oriented strand board, cellulose, cotton, lignin, and hemicellulose.

59. A structure or consumable device comprising the cellulosic material or article of claim 57.

60. An aqueous composition comprising in admixture (a) a complex comprising (i) molybdate ions, tungstate ions or a mixture thereof, and (ii) copper ions, zinc ions or a mixture thereof; and (b) ammonia, or a mixture of ammonia and an ethanolamine; wherein component (b) is present in an amount sufficient to solubiilize the complex; and wherein a molybdate ion, when present in component (a), is present in the absence or substantial absence of a quaternary ammonium salt.

61. The composition of claim 60 wherein component (b) comprises ammonia.

62. The composition of claim 60 wherein component (b) comprises a mixture of ammonia and an ethanolamine.

63. The composition of claim 60 further comprising at least one hydrolyzed olefin/maleic anhydride copolymer.

64. The composition of claim 60 further comprising a copper chelating compound.

65. The composition of claim 60 further comprising a component (c) selected from one or both of an additional antifungal component and an additional a termiticidal component.

66. A process for preserving cellulosic material, or an article that comprises cellulosic material, comprising contacting the cellulosic material or the article with the composition of claim 60.

67. The process of claim 66 wherein the cellulosic material is selected from the group consisting of wood, lumber, plywood, oriented strand board, cellulose, hemicellulose, lignin, cotton, and paper.

68. The process of claim 66 which comprises dipping, brushing, spraying, draw-coating, rolling or pressure-treating the cellulosic material or article with the composition.

69. Cellulosic material, or an article comprising cellulosic material, wherein the composition of claim 60 is adsorbed on and/or absorbed in the cellulosic material.

70. The material or article of claim 69 wherein the cellulosic material is selected from the group consisting of wood, lumber, plywood, oriented strand board, cellulose, cotton, lignin, and hemicellulose.

71. A structure or consumable device comprising the cellulosic material or article of claim 69.

* * * * *